(12) United States Patent
Mohr, Jr. et al.

(10) Patent No.: US 11,175,202 B2
(45) Date of Patent: Nov. 16, 2021

(54) APPARATUS AND METHOD FOR COLLECTING ENVIRONMENTAL SAMPLES

(71) Applicants: Arthur W Mohr, Jr., Bloomfield, MI (US); David Barron, Ann Arbor, MI (US); Kyle Andrew Dorosz, Lake Orion, MI (US)

(72) Inventors: Arthur W Mohr, Jr., Bloomfield, MI (US); David Barron, Ann Arbor, MI (US); Kyle Andrew Dorosz, Lake Orion, MI (US)

( * ) Notice: Subject to any disclaimer, the term of this patent is extended or adjusted under 35 U.S.C. 154(b) by 568 days.

(21) Appl. No.: 15/732,810

(22) Filed: Jan. 2, 2018

(65) Prior Publication Data
US 2019/0204189 A1    Jul. 4, 2019

(51) Int. Cl.
| | |
|---|---|
| *B64C 29/00* | (2006.01) |
| *G01N 1/22* | (2006.01) |
| *B64C 39/02* | (2006.01) |
| *G05D 1/00* | (2006.01) |
| *G01N 21/00* | (2006.01) |
| *G01N 33/00* | (2006.01) |
| *G05D 1/10* | (2006.01) |
| *G01N 1/24* | (2006.01) |
| *G01N 1/02* | (2006.01) |

(52) U.S. Cl.
CPC ......... *G01N 1/2294* (2013.01); *B64C 39/024* (2013.01); *G01N 21/00* (2013.01); *G01N 33/00* (2013.01); *G05D 1/0094* (2013.01); *B64C 2201/108* (2013.01); *B64C 2201/12* (2013.01); *G01N 1/24* (2013.01); *G01N 2001/021* (2013.01); *G01N 2001/2291* (2013.01); *G05D 1/102* (2013.01)

(58) Field of Classification Search
CPC ...... G01N 1/2294; G01N 33/00; G01N 21/00; G01N 2001/021; G01N 1/24; G01N 2001/2291; G01N 33/0004; G05D 1/0094; G05D 1/102; G05D 1/0646; B64C 39/024; B64C 2201/12; B64C 2201/108; B64C 2201/123
See application file for complete search history.

(56) References Cited

U.S. PATENT DOCUMENTS

| | | |
|---|---|---|
| 6,694,067 B1 | 2/2004 | O'Keefe |
| 6,795,190 B1 | 9/2004 | Paul |
| 6,839,140 B1 | 1/2005 | O'Keefe |
| 7,073,748 B2 | 7/2006 | Maurer |
| 7,096,749 B2 | 8/2006 | Schimmoller |

(Continued)

OTHER PUBLICATIONS

NPL Volcano Volcano Plume Measurements using a UAV for the 2014 Mt Ontake eruption (Year: 2016).*

(Continued)

*Primary Examiner* — Masud Ahmed
(74) *Attorney, Agent, or Firm* — James Wiegand

(57) ABSTRACT

An unmanned aerial vehicle detector includes an unmanned aerial vehicle, a pump/detector combination on the unmanned aerial vehicle and a tube including a rigid section and a flexible section. The tube is connected at a proximal end to the pump/detector combination. The pump/detector combination is configured to draw gas samples from a distal end of the tube to the detector and to detect a level of a gas drawn from within a prescribed distance above ground level.

20 Claims, 18 Drawing Sheets

(56) References Cited

U.S. PATENT DOCUMENTS

| | | |
|---|---|---|
| 7,298,490 B2 | 11/2007 | Baer |
| 7,468,797 B1 | 12/2008 | O'Keefe |
| 7,841,563 B2 | 11/2010 | Goossen |
| 7,998,731 B2 | 8/2011 | Daitch |
| 8,654,334 B1 | 2/2014 | Gupta |
| 8,820,672 B2 | 9/2014 | Erben |
| 9,671,332 B2 | 6/2017 | Christensen |
| 10,175,151 B2 * | 1/2019 | Avakov ................ G01N 1/2273 |
| 10,179,647 B1 * | 1/2019 | Meugnier ............. B64C 39/024 |
| 2014/0204382 A1 | 7/2014 | Christensen |
| 2014/0319352 A1 | 10/2014 | Gupta |
| 2016/0364989 A1 * | 12/2016 | Speasl .................... G06Q 10/08 |
| 2017/0010624 A1 * | 1/2017 | Carpenter ............. B64C 39/024 |
| 2017/0328814 A1 * | 11/2017 | Castendyk ............. G01N 33/18 |
| 2017/0369168 A1 * | 12/2017 | Hwang .................... A61L 9/14 |
| 2018/0259429 A1 * | 9/2018 | Adams ................. B64C 39/024 |
| 2019/0059724 A1 * | 2/2019 | Astigarraga .......... B64C 39/024 |

OTHER PUBLICATIONS

NPL Water Drone "Water-Slurpingdroneshave Broadpotential" (Year: 2014).*

Development and Validation of a UAV Based System for Air Pollution Measurements (Year: 2016).*

* cited by examiner

APPARATUS AND METHOD FOR COLLECTING ENVIRONMENTAL SAMPLES

RELATED APPLICATIONS

This application claims benefit of U.S. Provisional Application No. 62/441,956, filed Jan. 3, 2017, which is hereby incorporated by reference in its entirety.

BACKGROUND

Inventive concepts relate to a system and method for collecting ground-level environmental samples, such as ground-level gas samples. In particular, inventive concepts relate to systems and methods that employ an unmanned vehicle, such as an unmanned aerial vehicle (UAV), for collecting ground-level environmental samples.

Conventionally, ground-level gas samples require a human operator to haul an analysis device over a tract of interest, such as a landfill site, in order to sample gas concentrations at ground-level (which may be up to four inches above the ground surface level). The analysis device may be a flame ionization detector, a photo ionization detector, or tunable diode laser detector attached to an environmental sampling tube, for example. The detector includes a pump to create a low pressure region within the sampling tube to thereby continually draw in gaseous samples from the inlet end of the sampling tube. The gaseous samples travel up the sampling tube and into the detector for analysis.

Collection of the gaseous samples can be either continuous or discrete. In continuous sampling, the pump is constantly pulling in sampled air into the receiving unit for either storage in a plurality of discrete containers or the continuous stream of samples may continually be analyzed in near real time by one or more analysis systems carried by the human operator. In discrete sampling, the pump is normally off until reaching a distinct point in time and/or space at which a sample is desired to be taken. At that point, the pump is activated to pull sampled air into the receiving unit for either storage in a discrete container or analysis within an analysis unit. The time and location of the sample is typically recorded.

In landfill monitoring applications, gas emissions may be monitored to ensure that a landfill capping membrane remains intact and that no harmful gases, such as methane, are being released into the environment. In such applications a human operator must haul the detector and sampling tube in a serpentine pattern over the land area (for example, landfill) requiring analysis. Environmental regulatory agencies typically require continuous sampling, with no single point within the examined area to be more than 5 meters from another sampled location. To address this requirement, a sampling course (also referred to herein, simply, as a "course") may be of a serpentine pattern, with paths spaced every 10 meters. Particular attention may be paid to turns at the end of each path in order to ensure rounded paths do not leave interstitial points greater than 5 m from the sampling path. By integrating a global positioning system (GPS) into the detector assembly and mapping the serpentine paths within the sampling area with the GPS, while simultaneously taking continuous environmental samples, an operator certifies compliance with the agency regulation. That is, the environmental sample data is correlated with the GPS data to verify that samples have been taken with the required spatial resolution.

Many environmental regulatory agencies also require additional sampling in areas of high interest, for instance ground vents, valves, openings in ground covering and around areas whose sample exceeds a pre-defined threshold, for instance 500 ppm of methane, during a sampling session. In such instances, sampling deviates from the serpentine pattern to collect higher fidelity data points in closer proximity to one-another than the standard 5 meters, for the purpose of determining the exact location of higher concentration substances.

These deviations from the serpentine pattern include sampling around many different types of obstacles such as bushes, brush, buildings, above ground tubes, and overhanging decks, for example. An operator can adjust his/her body position to orient the environmental sampling tube as needed; typically the human hand can manually position the inlet of the tube in the exact location desired, despite the presence of an obstacle. This manual method however is not conducive to operator safety, as the operator is continually required to bend over, push through obstructing vegetation, and, sometimes, crawl beneath overhanging obstacles.

In addition to causing harm to the vegetation, the operator is put in a situation of high risk to bodily injury due to ergonomic issues or environmental hazards. For example, thorny vegetation, ankle-twisting ruts, or overhead obstructions that my pose a risk of head trauma. A walking operator without machine assistance also has an inherent risk of injury due to slips, trips and falls as well as injury due to operator fatigue; this risk of injury is an additional cost risk that must be factored into the value proposition of an operator carried near ground environmental sampling method. A human operator without machine assistance will also be unable to traverse extremely rugged terrain such as steep slopes, deep semi-solid terrain (such as marshes), etc. When carried by an operator, the detector system is limited to the speed of the operator's walking pace (with a typical max of 1.4 meters per second/3.1 miles per hour).

An improved system and method for sampling ground-level gaseous emissions would therefore be desirable.

SUMMARY OF THE INVENTION

In example embodiments in accordance with principles of inventive concepts an unmanned aerial vehicle detector includes an unmanned aerial vehicle, a pump/detector combination on the unmanned aerial vehicle; and a tube including a rigid section and a flexible section connected at a proximal end to the pump/detector combination, wherein the pump/detector combination is configured to draw gas samples from a distal end of the tube to the detector and to detect a level of a gas drawn from within a prescribed distance above ground level.

In example embodiments in accordance with principles of inventive concepts, an unmanned aerial vehicle detector includes a geolocation unit configured to determine the geolocation of the unmanned aerial vehicle; and a controller configured to determine the location from which a gas sample is obtained.

In example embodiments in accordance with principles of inventive concepts, an unmanned aerial vehicle detector includes an imager configured to image terrain proximate the unmanned aerial vehicle.

In example embodiments in accordance with principles of inventive concepts, an unmanned aerial vehicle detector includes a visible light range imager.

In example embodiments in accordance with principles of inventive concepts, an unmanned aerial vehicle detector includes an infrared light range imager.

In example embodiments in accordance with principles of inventive concepts, an unmanned aerial vehicle detector includes a controller configured to direct the unmanned aerial vehicle detector along a course that surveys a tract satisfying a maximal sample-separation course requirement.

In example embodiments in accordance with principles of inventive concepts, an unmanned aerial vehicle detector includes a controller configured to redirect the unmanned aerial vehicle along a localization course, whereby the source of gas emission may be more precisely located, when the detector detects a gas of interest at a level that exceeds a threshold.

In example embodiments in accordance with principles of inventive concepts, an unmanned aerial vehicle gas sampling method includes an unmanned aerial vehicle flying over a tract of interest; and a pump/detector combination on the unmanned aerial vehicle drawing gas samples through a tube including a rigid section and a flexible section connected at a proximal end to the pump/detector combination, wherein the pump/detector combination is configured to draw gas samples from a distal end of the tube to the detector and to detect a level of a gas drawn from within a prescribed distance above ground level.

In example embodiments in accordance with principles of inventive concepts, an unmanned aerial vehicle gas sampling method includes a geolocation unit determining the geolocation of the unmanned aerial vehicle; and a controller determining the location from which a gas sample is obtained.

In example embodiments in accordance with principles of inventive concepts, an unmanned aerial vehicle gas sampling method includes an imager imaging terrain proximate the unmanned aerial vehicle.

In example embodiments in accordance with principles of inventive concepts, an unmanned aerial vehicle gas sampling method includes an imager imaging in visible light range.

In example embodiments in accordance with principles of inventive concepts, an unmanned aerial vehicle gas sampling method includes an imager imaging in an infrared light range.

In example embodiments in accordance with principles of inventive concepts, an unmanned aerial vehicle gas sampling method includes a controller directing the unmanned aerial vehicle detector along a course that surveys a tract satisfying a maximal sample-separation course requirement.

In example embodiments in accordance with principles of inventive concepts, an unmanned aerial vehicle gas sampling method includes a controller redirecting the unmanned aerial vehicle along a localization course, whereby the source of gas emission may be more precisely located, when the detector detects a gas of interest at a level that exceeds a threshold.

In example embodiments in accordance with principles of inventive concepts, an unmanned aerial vehicle gas sampling system includes an unmanned aerial vehicle, including: a pump/detector combination on the unmanned aerial vehicle; a tube including a rigid section and a flexible section connected at a proximal end to the pump/detector combination, wherein the pump/detector combination is configured to draw gas samples from a distal end of the tube to the detector and to detect a level of a gas drawn from within a prescribed distance above ground level; a wireless communication system; and an external controller configured to receive gas detection data transmitted from the unmanned aerial vehicle and to store the gas detection data.

In example embodiments in accordance with principles of inventive concepts, an unmanned aerial vehicle gas sampling system includes an external controller configured to track gas detector data for a plurality of detection sessions.

In example embodiments in accordance with principles of inventive concepts, an unmanned aerial vehicle gas sampling system includes an external controller configured to receive imaging data from the unmanned aerial vehicle.

In example embodiments in accordance with principles of inventive concepts, an unmanned aerial vehicle gas sampling system includes an external controller configured to correlate imaging with gas detection data from the unmanned aerial vehicle.

In example embodiments in accordance with principles of inventive concepts, an unmanned aerial vehicle gas sampling system includes an external controller configured to correlate near infrared imaging data from the unmanned aerial vehicle with gas detection data from the unmanned aerial vehicle.

In example embodiments in accordance with principles of inventive concepts, an unmanned aerial vehicle gas sampling system includes an unmanned aerial vehicle gas detection server.

BRIEF DESCRIPTION OF THE DRAWINGS

Exemplary embodiments in accordance with principles of inventive concepts will be more clearly understood from the following detailed description taken in conjunction with the accompanying drawings in which.

DETAILED DESCRIPTION

Figure 1:
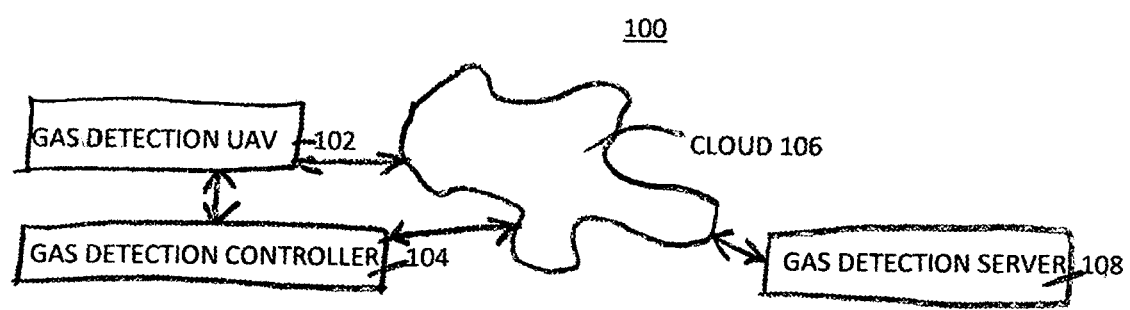
FIG. 1 is conceptual block diagram of an example embodiment of an unmanned aerial vehicle gas detections system in accordance with principles of inventive concepts.

Exemplary embodiments in accordance with principles of inventive concepts will now be described more fully with reference to the accompanying drawings, in which exemplary embodiments are shown. Exemplary embodiments in accordance with principles of inventive concepts may, however, be embodied in many different forms and should not be construed as being limited to the embodiments set forth herein; rather, these embodiments are provided so that this disclosure will be thorough and complete, and will fully convey the concept of exemplary embodiments to those of ordinary skill in the art. Like reference numerals in the drawings denote like elements, and thus their description may not be repeated.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein the term "and/or" includes any and all combinations of one or more of the associated listed items. Other words used to describe the relationship between elements should be interpreted in a like fashion (for example, "between" versus "directly between," "adjacent" versus "directly adjacent," "on" versus "directly on"). The word "or" is used in an inclusive sense, unless otherwise indicated.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of exemplary embodiments.

Spatially relative terms, such as "beneath," "below," "lower," "above," "upper," "top," "bottom," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if an element in the figures is turned over, elements described as "bottom," "below," "lower," or "beneath" other elements or features would then be oriented "atop," or "above," the other elements or features. Thus, the exemplary terms "bottom," or "below" can encompass both an orientation of above and below, top and bottom. The device may be otherwise oriented (rotated 90 degrees or at other orientations) and the spatially relative descriptors used herein interpreted accordingly.

The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which exemplary embodiments in accordance with principles of inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

A gas detection system in accordance with principles of inventive concepts may employ an unmanned aerial vehicle (UAV) that flies a predetermined, or determined in real time, path over a tract of interest, such as a landfill. The UAV includes a collection tube connected at a first end to a pump that draws samples from a second end of the tube to a detector on board the UAV. The second end of the collection tube trails behind the vehicle along the ground at no more than a prescribed height (four inches in a landfill monitoring application). The pump and collection tube are constructed and arranged to collect ground-level gas samples as the UAV traverses a tract of interest (a landfill, for example). In example embodiments gas is propelled up the tube to a gas detector, such as a flame ionization detector, which analyzes the gas content and determines the levels (in parts per million, for example) of the constituent gases within a collected sample. In example embodiments a gas detection system in accordance with principles of inventive concepts may employ any type of UAV, including, but not limited to those that employ horizontally rotating rotors for lift and propulsion (e.g., quadcopters), fixed wing, airship (e.g., a lighter-than-air rigid on non-rigid airship such as a blimp dirigible), or any combination of such flight technologies.

In example embodiments, gases may be collected continuously, as the gas-detecting UAV flies uninterrupted along a predetermined path, or it may be collected intermittently, sampling only at predetermined intervals along a flight path. Whether employing intermittent or continuous sampling, the pump may be operated continuously, with gas samples gated or shunted off for the intermittent sampling approach. Alternatively, for intermittent collection, the pump may be shut off between collection points.

Using a continuous sampling approach a steady flow of gas, pumped from ground-level through the collection tube and to the detector, reaches the detector, with the continuous volume flow rate of gas quantized by detector output frequency corresponding to a specific location at the surface of the ground below. In such embodiments, to a first order, the location from which the gas sample was obtained may be determined from knowing the gas transport time (that is, the time required for gas to travel from one end of the collection tube to the other), detector analysis time, the position of the second end (the collecting end) of the collection tube relative to the UAV, velocity of the UAV and terrain traversed by the UAV. Knowing these things, the ground-location of the gas sample relative to the gas collection UAV may be converted to a "universal" location (a geolocation, for example) using the UAV's GPS location and the offset thus computed.

When operating in a continuous mode over uniform terrain, gas may be pumped to the gas detector at the same rate as the UAV traverses the tract of land. As a result, a steady flow of gas reaches the detector and the ground location from which a gas sample has been obtained may be determined by adding a simple lag factor (e.g., the time for gas to travel the length of the tube) to the UAV's time and time dependent position information.

A gas collection system in accordance with principles of inventive concepts may employ a gas collection tube of a length no greater than that required to accommodate variations in a tract's terrain. In such embodiments, if gas samples are propelled along a collection tube at a sufficiently high rate, samples are obtained virtually instantaneously and, with a short enough collection tube, the location of the tube inlet (and sample) is substantially the same as that of the UAV.

Additionally, any uncertainty introduced into the location of a gas source may be somewhat ameliorated by using a more precise locating approach once a gas emission source within a predetermined range of a proscribed threshold is detected. That is, once a gas concentration threshold (which may be less than that required by statute) is passed, the UAV may break off from its predetermined "serpentine" search to more precisely locate the source of the threshold-exceeding gas emission.

One exemplary approach, described in greater detail below, is for the UAV to ascend to a position above ground-level (as determined, for example, by onboard LIDAR) where the gas detection tube is substantially vertical, the gas detection tube inlet is within a prescribed range of ground-level, and the gas detection tube is substantially directly below the gas detection UAV (and therefore shares its GPS coordinates). That is, in instances where the UAV is operating in rough terrain, the UAV may not be able to accommodate rapid variations in ground-level and the gas collection tube may not trail the UAV at a consistent distance; when the UAV encounters a sudden drop in the terrain, the UAV may not be able to descend rapidly and, as a result the vertical distance between the UAV and the distal, collection, end of the collection tube may suddenly increase. One approach to addressing rapid variation in terrain levels, as described in greater detail below, is to raise the UAV to a height above ground level just beyond the length of the collection tube. In such embodiments, the distal, or collection, tube end directly below the UAV and the sample's coordinates are identical to those of the UAV.

A gas detection and analysis system in accordance with principles of inventive concepts may include a gas detection unmanned aerial vehicle (UAV), a gas detection UAV controller, and a gas detection server. In example embodiments a gas detection UAV may include, in addition to the vehicle itself: a gas pump, an inlet tube, and a UAV processor. The UAV processor may be configured to determine the location of the UAV using, for example, a global positioning system (GPS) receiver, local beacons, or other electronic location devices and services. The UAV processor may also include communications, data processing and storage, vehicle attitude, velocity, and altitude and terrain-following devices and processes to be described in greater detail below. Although any of a variety of gas detectors may be employed, such as catalytic oxidation, flame ionization, infrared absorption, or photoionization detector, for example, for brevity and clarity of description example embodiments will be described as employing flame ionization detectors.

The gas detection UAV controller may be configured to transmit gas detection alarms, flight metrics, battery status indicators, gas readings, etc. all of which may be used in real time to determine the flight path. Flight control of the UAV may be autonomous, under direct control of an operator (using a UAV controller, for example), or a combination thereof. In example embodiments a gas detection UAV, either autonomously or in combination with operator input via a gas detection UAV controller may initiate a ground-level gas inspection session by obtaining a sufficiently high altitude to obtain a view of the entire site to be monitored. Using an overview such as this a gas detection UAV in accordance with principles of inventive concepts may generate a detection course that, in a landfill inspection embodiment, yields the required sampling density (no point greater than five meters from a sampled location, for example). Such as course may be generated on site, retrieved from a previous detection session, or a modification from a previous course and may include waypoints to guide the gas detection UAV along the course.

Because a gas detection UAV in accordance with principles of inventive concepts is not sensitive to variations in terrain in the way that a terrestrial detection system is, the course may be much more regular, much more efficient and much more cost-effective. For example, a UAV gas detection system in accordance with principles of inventive concepts may employ a substantially rectilinear, or grid-based, path, as described in greater detail below. Other embodiments are contemplated within the scope of inventive concepts, such as spiral paths, concentric circular paths, or other forms, for example. In accordance with principles of inventive concepts, a gas detector UAV may modify a course previously employed on a given site by, for example, plotting a course that is at an angle (for example, forty-five degrees, ninety degrees, one hundred and thirty five degrees, etc.) to the retrieved course.

A gas detection server in accordance with principles of inventive concepts may store, analyze and process data received from a gas detection UAV or gas detection UAV controller and may communicate with a gas detection UAV, gas detection UAV controller or with other electronic devices, such as computer notebooks, computer tablets, computer phablets, or smartphones, for example. A system in accordance with principles of inventive concepts may analyze gas detection data over time (for example, over a plurality of detection operations) to identify trends and to predict future gas emissions. Based upon its analyses, a system in accordance with principles of inventive concepts may propose prophylactic measures. Such analyses may be carried out on any single system element including a processor (UAV processor, UAV controller, or gas detection server) or any combination of system elements. A system and method in accordance with principles of inventive concepts may correlate near-infrared (IR) or other image data, or other data, with gas detection data to form a comprehensive view of an area's foliage and relate that to gas leaks. That is, for example, near-infrared imagery may reveal chlorophyll levels in plants on the site and such levels may be related to the health of a plant, which, in turn, may be related to gas emissions, such as methane emissions. As a result, a system and method in accordance with principles of inventive concepts may employ various forms of imagery, such as near-infrared imagery, to supplement findings obtained by a gas detection scan of a site.

Although a variety of gases may be detected and processed, for brevity and clarity of description the following discussion will focus primarily on the detection and processing of methane gas data.

In the block diagram of FIG. 1 a gas detection system 100 in accordance with principles of inventive concepts includes a gas detection UAV 102, a gas detector UAV external controller 104 and a gas detector server 108. Various elements of the system 100 may communicate directly with one another or through the cloud 106, for example. Gas detector UAV external controller 104 may be implemented as a computer notebook, computer tablet, computer phablet, or smartphones, for example and may include display, input/output interface, and transceivers, such as wireless transceivers, for example. The gas detector UAV external controller 104 may be configured and arranged in accordance with principles of inventive concepts to map out a course for gas detector UAV 102, including waypoints, to display and store gas detection data in various raw, processed and reduced configurations and to exchange raw, processed, and reduced gas detection (including, for example, multi-spectral imaging data) with gas detection server 108 through cloud 106, for example. Gas detector UAV external controller 104 may be used on-site with an operator to exercise control over gas detector UAV 102, to monitor the progress of a gas detector UAV 102 as it executes a site inspection and to intervene, as necessary. Communications between gas detector UAV 102 and gas detector UAV external controller 104 may be implemented using a wireless communication link, for example.

Figure 2:
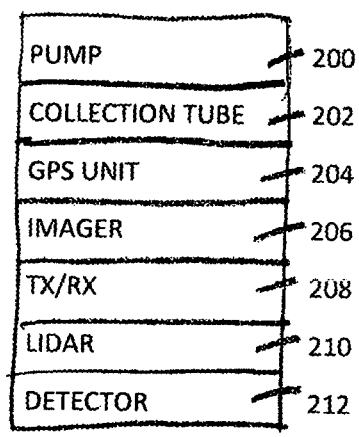
FIG. 2 is a conceptual block diagram of an example unmanned aerial gas detector in accordance with principles of inventive concepts.

Elements of an example embodiment of a UAV 102 in accordance with principles of inventive concepts are depicted in greater detail in the block diagram of FIG. 2. In addition to flight control, props, motors, and, optionally, lighter than air containment vessels, a gas detection UAV 102 in accordance with principles of inventive concepts may include a pump 200, a collection tube 202, a geolocation unit 204, imager(s) 206, a communications unit 208, detector(s) 212, and a range finder 210. Pump 200 is connected to collection tube 202 to pull gas samples from near-ground-level (no more than 4 inches above ground-level in example embodiments) through collection tube 202 and in to detector 212.

In example embodiments pump 200 may be Of numerous operating methods including but not limited to centrifugal, peristaltic, etc., consuming 0.1 W to 100 watts of power to create a vacuum pressure differential collection tube may be of numerous materials including but not limited to vinyl, poly vinyl chloride, EPDM, silicone, latex, with conductive or insulating properties and diameter of 1 to 25 mm and length of 3 to 10 m that results in a flow rate of up to 200 liters per hour resulting in a time to transport gas samples through the sample tube of 0.1 to 20 seconds. In example embodiments gas collection tube 202 may include a flexible section at its proximal, pump, end and a rigid section at its distal, collection end. This combination effectively creates a "hinged" collector tube that permits movement over ground-level obstructions while maintaining a relatively close proximity to the ground. Experimental use has demonstrated that the weight of the rigid section of the tube is sufficient to keep the tube inlet close to the ground while passing over obstructions; one particular study with a 1 meter rigid section of carbon fiber tube of ½ inch inner diameter coupled to a 4 meter flexible section of 3/16 inch inner diameter static dissipating (electrically conductive to reduce probability of conducted shock to the sensor) silicone tubing with UAV operating between 5 and 15 knots at 3 meters above ground level substantially reduced bouncing at the distal end of the rigid section such that gas samples were taken below 4 inches above ground level.

Geolocation unit 204 may be a global positioning system (GPS) or other electronic geolocation system that electronically determines the location of the unit 204 and the UAV to which it is attached. Geolocation unit 204 may, additionally, provide a time/date stamp, which gas detecting UAV 102 may employ in its logging and analysis of gas emissions. In accordance with principles of inventive concepts a gas detection UAV 102 may include one or more imagers that may provide multispectral imaging of a tract that is being surveyed for gas emissions.

Images of various spectra may include visible and near infrared, for example. As will be described in greater detail below, images from different spectral ranges may be employed to locate areas of gas emissions and to identify areas that may be of particular interest or concern for future emissions. Near-infrared images may, for example, reveal plant stress and such plant stress may be due to gas emissions, such as methane emissions. By identifying areas of stressed plants, a system and method in accordance with principles of inventive concepts may be able to focus on areas of concern for more precise gas detection and amelioration. Communications unit 208 may provide wireless communications through any of a variety of channels such as IEEE 802.15 (e.g., Bluetooth®) IEEE 802.11 (e.g., WiFi), packetized radio frequency (e.g. RFM6X LoRa, etc), for example to a gas detector UAV external controller 104 or, through cloud 106 to a gas detection UAV server, for example. Range finder 210 may be a light detection and ranging (LIDAR) unit for example, and may be used to determine the distance above ground-level of gas detection UAV 102. This distance may be used, in turn, to more precisely determine the "horizontal" distance between the UAV 102 and the inlet of collection tube 202. In example embodiments in accordance with principles of inventive concepts gas detector 212 may be a catalytic oxidation, flame ionization, infrared absorption, or photoionization detector, for example. Range finder 210 may also be used to determine other distances associated with UAV and may be gimbal-mounted on the UAV in order to enable ranging in multiple directions, for example.

Figure 3:
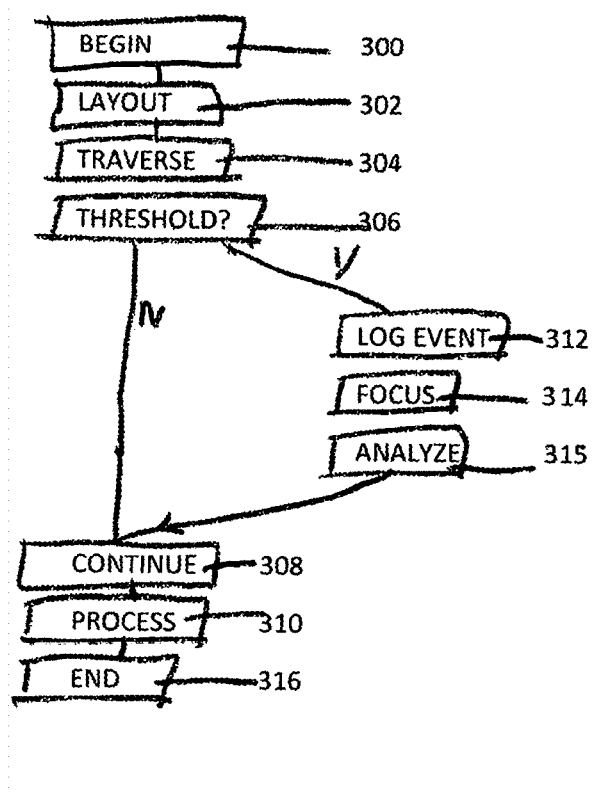
FIG. 3 is a flow chart of an example embodiment of a gas detection session in accordance with principles of inventive concepts.

The flow chart of FIG. 3 illustrates an example method of gas detection in accordance with principles of inventive concepts. The process begins in step 300 and proceeds from there to step 302, where a detection course for a particular site, such as a landfill site, is created or retrieved. In accordance with principles of inventive concepts, the course could be newly-generated, automatically, by UAV 102 and UAV external controller 104, for example, or may be retrieved from a library of courses. As previously mentioned, a system 100 in accordance with principles of inventive concept may take advantage of the relative immunity to challenging terrain by developing more direct (for example, substantially rectilinear courses that crisscross the site in parallel lines) routes, other routes (spiraling or concentric circles, for example) or combinations (in parallel course lines in one direction one time and in parallel course lines at an angle to those course lines in a subsequent operation) that would be impractical using conventional approaches.

From step 302 the process proceeds to step 304, where a gas detection UAV 102 in accordance with principles of inventive concepts begins sampling gas along the detection course set in step 302. As previously described, gas sampling may be carried out continuously or intermittently.

Other data, in the form of various imaging data of any of a variety of spectra, for example, may also be obtained by the gas detection UAV 102 while traversing the detection course. As previously indicated, imaging data may include visible range or near infrared range imaging data that a system in accordance with principles of inventive concepts may employ to correlate with gas emission data to diagnose and predict gas emissions and their levels. Imaging data may also be used to aid an operator in visualizing the terrain being covered and potential gas sources and their locations.

As the gas detection UAV 102 traverses the gas detection course, monitors gas detection data and images the landscape, in example embodiments it provides course tracking information, for example, to a gas detection UAV external controller 104 so that an operator may monitor progress of the gas sampling process. Gas detection, imaging, time and location data may be transmitted from gas detection UAV 102 to gas detection UAV external controller 104 or gas detection server 108 on a regular, substantially continuous basis, for example. Various data processing, data reduction, and data analyses may be performed by processors in the UAV 102, external controller 104 or server 108 during and after the gas emission data collection process.

As the course is being traversed by the UAV 102 gas levels (for example, methane levels) are compared to a threshold level, which may be less than a statutorily permissible level, as in step 306 and, so long as the threshold level is not exceeded, the UAV 102 continues along its detection course (step 308). Should a gas sample exceed the predetermined threshold level, the process proceeds from step 306 to step 312 where an exceedance is logged and the UAV 102 proceeds to determine the exact source of the threshold-exceeding gas sample. To more precisely locate the source of the emission the UAV 102 may divert from the gas detection course to follow a different, localization course. In example embodiments a localization course may involve spiraling outward from the initial exceedance location, gathering gas and image data and locating a peak gas value, or interstitial rectilinear path(s) to collect spatially higher fidelity data between previously measured paths, or deviation to sample near local objects of interest (discolorations, man-made objects, etc) as identified using the aforementioned various forms of imagery for example. In step 314 image and gas detection data from this localization operation is used to focus on the cause of the exceedance. To that end, data may be stored in the UAV 102, transmitted to UAV external controller 104 or gas detection server 108, and may be employed for further analyses in accordance with principles of inventive concepts, for example in step 315, as described in greater detail below. From step 315 the process may proceed to step 308, and from there as previously described. As will be described in greater detail below, the gas detection course may be predetermined or developed in real time and may be based upon a prescribed maximal distance between gas samples, for example.

Figure 4:
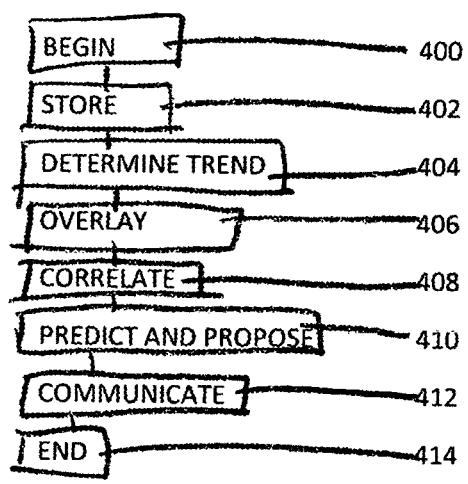
FIG. 4 is a flow chart of an example embodiment of a gas analysis process in accordance with principles of inventive concepts.

The flow chart of FIG. 4 depicts an example embodiment of a gas detection analysis method in accordance with principles of inventive concepts. The various steps of this method may be carried out by any one or any combination of elements of a system 100 in accordance with principles of inventive concepts (i.e., gas detection UAV 102, gas detection UAV external controller 104, or gas detection server 108). As previously indicated, various steps in the process may be carried out in orders different from those described here, some of the steps described here may not be included and other steps not described here may be added.

The example method begins in step 400 and proceeds from there to step 402, where gas emission data from a plurality of detection runs (for example, gas detection runs at the same site separated in time by an inspection schedule) for a given site are stored. In accordance with principles of inventive concepts, a complete set of gas reading data and image data may be stored. Conventionally, only data directly related to gas emission exceedances is employed in a gas detection log and other readings are discarded. In accordance with principles of inventive concepts, additional readings, those above a preset level (which could be as low as 0 ppm and, therefore, all readings) are stored for further analysis.

This additional data may be used in accordance with principles of inventive concepts to track readings for a particular site, to develop gas emission trends, to identify areas that may be susceptible to failure and to propose ameliorative actions. If, for example, readings of 200 ppm, 250 ppm, and 300 ppm of methane gas are logged over the course of three inspections at a particular location on a given site, a system and method in accordance with principles of inventive concepts may identify this trend (step 404), deduce that a small tear in a landfill membrane is growing and recommend that a site user proactively address the situation (step 410) before the EPA 500 ppm methane threshold is reached.

Similarly, imaging data, which may include data across a plurality of spectral ranges, may be stored and monitored to develop overlays (step 406), to identify trends (step 404) and to suggest prophylactic procedures (step 410). Imaging data may include near infrared imaging data, which may be correlated with chlorophyll levels in plant matter. A system and method in accordance with principles of inventive concepts may interpret the chlorophyll levels in terms of plant health and, particularly when cross-referenced with gas detection readings, may strengthen the interpretation of gas reading trends. In addition to storing the data and analytical results (in gas detection server 108, for example), results, recommendations and historical raw data (for one or more particular locations on a given site, for example) may be transmitted (step 412) to a gas detection UAV 102 or gas detection UAV external controller 104 for use in a current or future scan. Regions identified as potentially problematic (through increasing detected gas levels or image analysis) may then be more closely monitored by gas detection UAV 102 during a site inspection. The analytical process may continue (for example, returning to step 402 to store new data) or proceed to end in step 414.

Figure 5A:
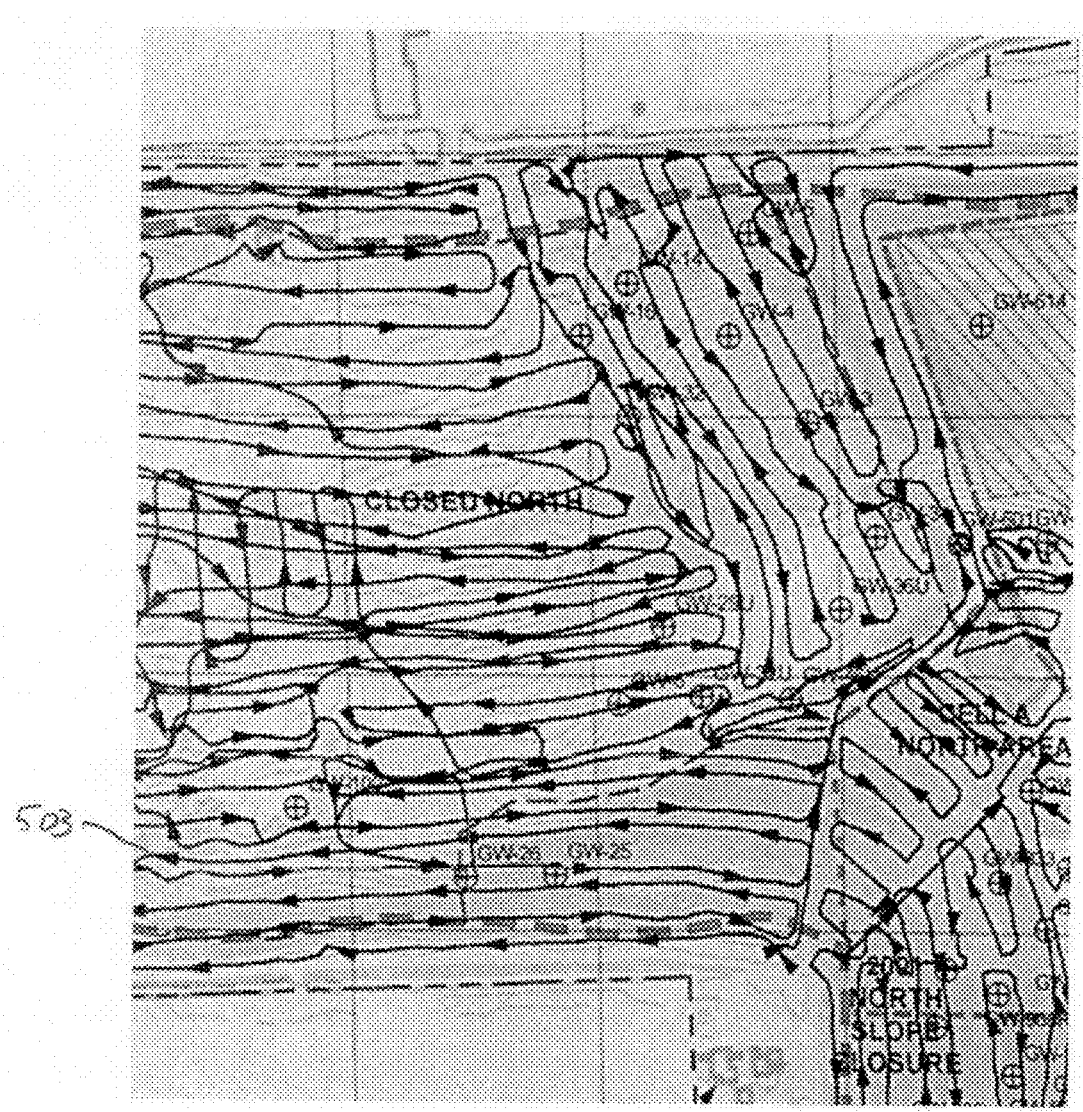
FIGS. 5A and 5B are depictions of conventional and inventive gas detection routes in accordance with principles of inventive concepts.
Figure 5B:
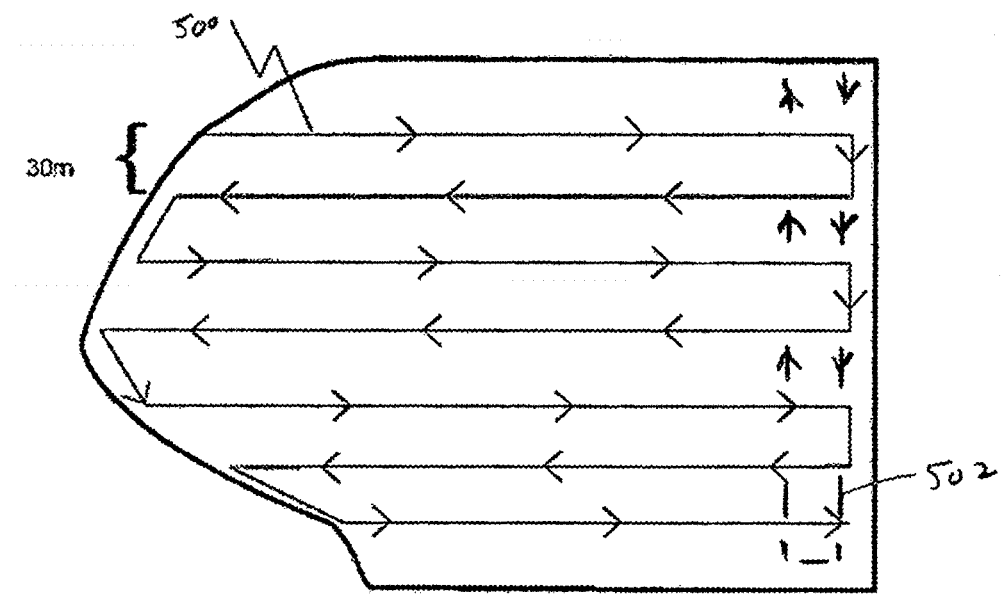

In example embodiments in accordance with principles of inventive concepts gas detection system 100 may layout detection courses, either autonomously or with assistance of an operator, along a grid system fitted to the outline of site to be tested. In a conventional approach, such as that of FIG. 5A, a course 503 may be laid out to accommodate terrain features, such as hills and valleys, as illustrated by the serpentine, overlapping course 503. However, a system 100 in accordance with principles of inventive concepts, substantially freed from the restrictions of a terrestrial inspection system, may employ a substantially rectilinear grid course 500 layout (see FIG. 5B) for increased efficiency. Additionally, a subsequent course 502 layout may be arranged at an angle to a current layout, with, for example, a second layout at ninety degrees to the first (dotted line 502 in FIG. 5B), a third course at forty-five degrees, a fourth at one hundred thirty five degrees, etc. In such a method in accordance with principles of inventive concepts, more complete coverage of a site and a more robust data set, in the form of both detected gas levels and imagery, may be developed.

Figure 6:
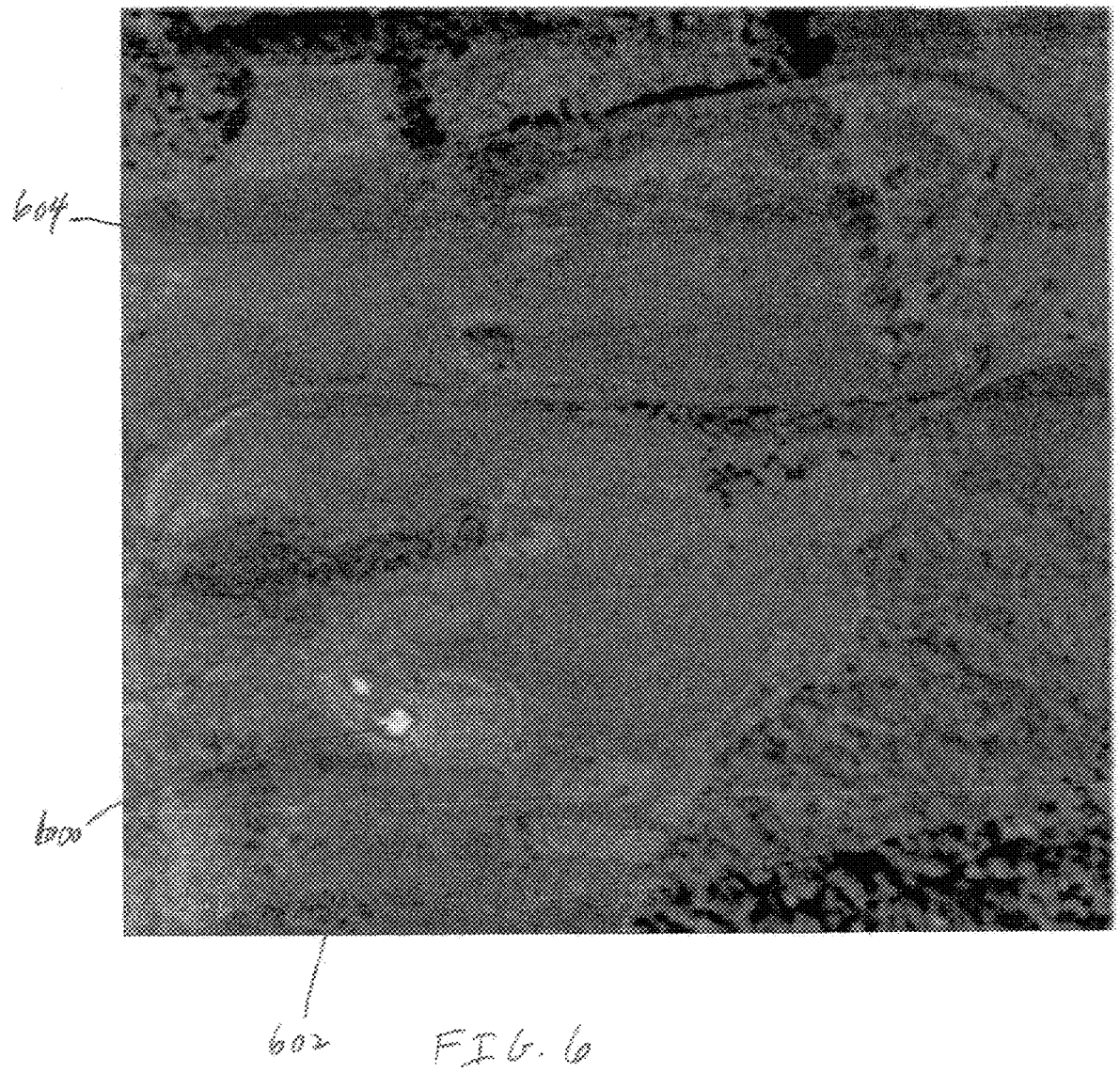
FIG. 6 is an example image in accordance with principles of inventive concepts that correlates imaging and gas detection data.

The image of FIG. 6 depicts a screen overlay, such as a near-infrared image overlay, which may be produced in accordance with principles of inventive concepts. Although this image is presented in grayscale, color may be used to enhance the image in accordance with principles of inventive concepts. In this image a "hot spot" 602 represents a region of high gas emissions. This may reflect both gas-emission and imagery data (e.g., near-infrared), for example. Nearby regions 602, of a different shade, reflect a lower gas emissions, which may also be informed by both gas detection data and imagery data. An even lower emission area 604 is depicted using another shade. A potential source of methane emission may be a valve head sticking up from the ground. Through experimentation it has been found that valve heads on landfills are usually encased in cement, which in some cases makes them settle to a larger extent than the surrounding ground cover. This could create concentric tears or thin sections in the ground covering and expose methane. Settling can occur based on different curvature of the landfill structure or the curvature can lead the ground covering to crack and expose methane.

Another potential source may be caused by insufficient material placed to encapsulate the covering. A section of the landfill could be filled with a particularly high concentration of biomass, emitting higher than normal methane which might manifest as a circle or oval gas penetrating the covering, for example.

As previously noted, a near-infrared image may be interpreted by a system in accordance with principles of inventive concepts to reveal chlorophyll levels in plant life and, in turn, the presence of gases, such as methane. Methane levels may be correlated with chlorophyll levels and employed by a system in accordance with principles of inventive concepts to supplement detected gas-level readings and to provide visual feedback to operators in the field and to landfill site managers, for example. In order to present imagery such as that of FIG.6, a system in accordance with principles of inventive concepts may employ geometric correction (e.g., orthorectification) to generate an orthomosaic image that is geometrically corrected so that the scale of elements within the image is consistent across the image.

Figure 7A:
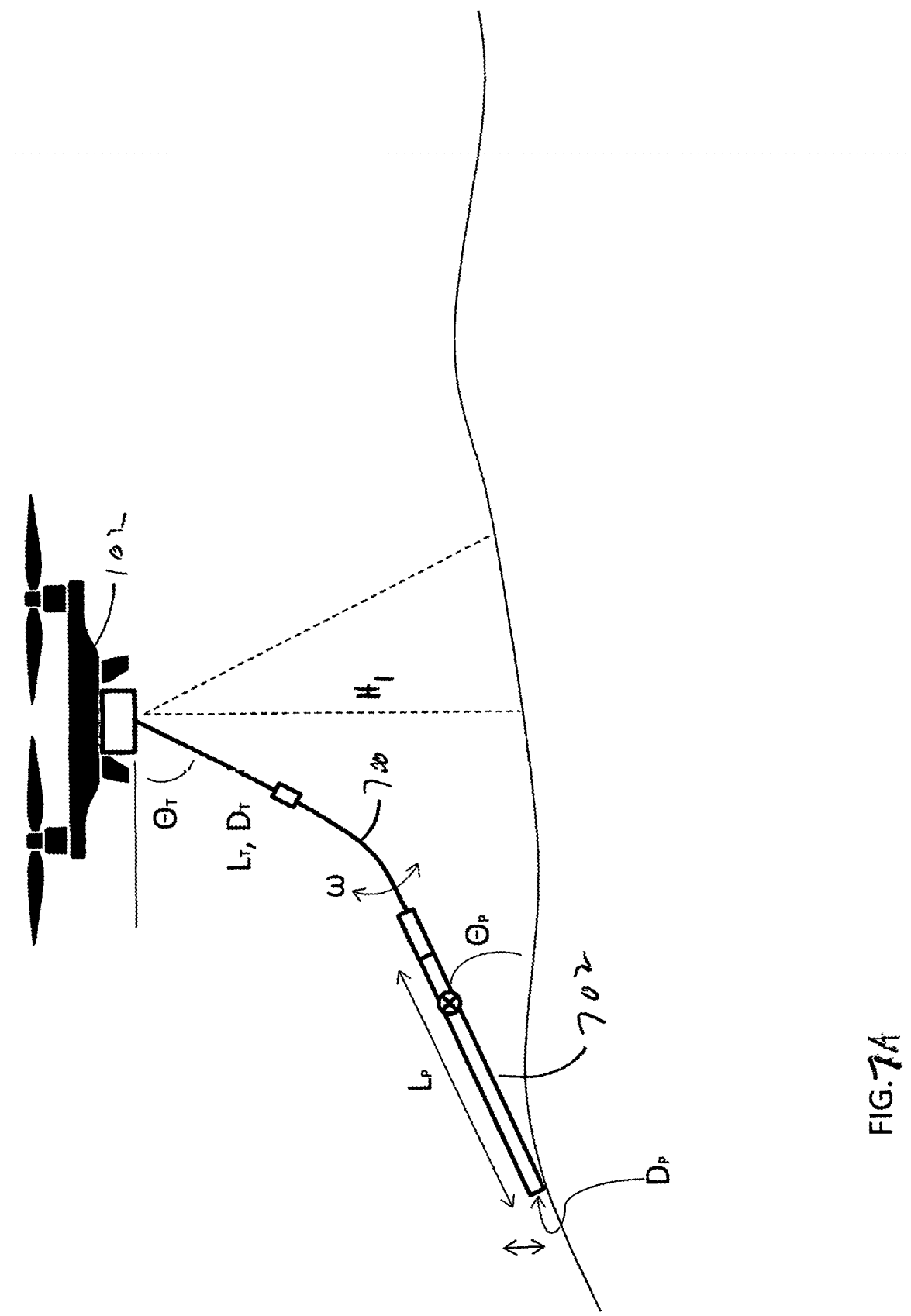
FIG. 7A and 7B are example diagrams of an unmanned aerial detector in operation in accordance with principles of inventive concepts over a varying terrain.
Figure 7B:
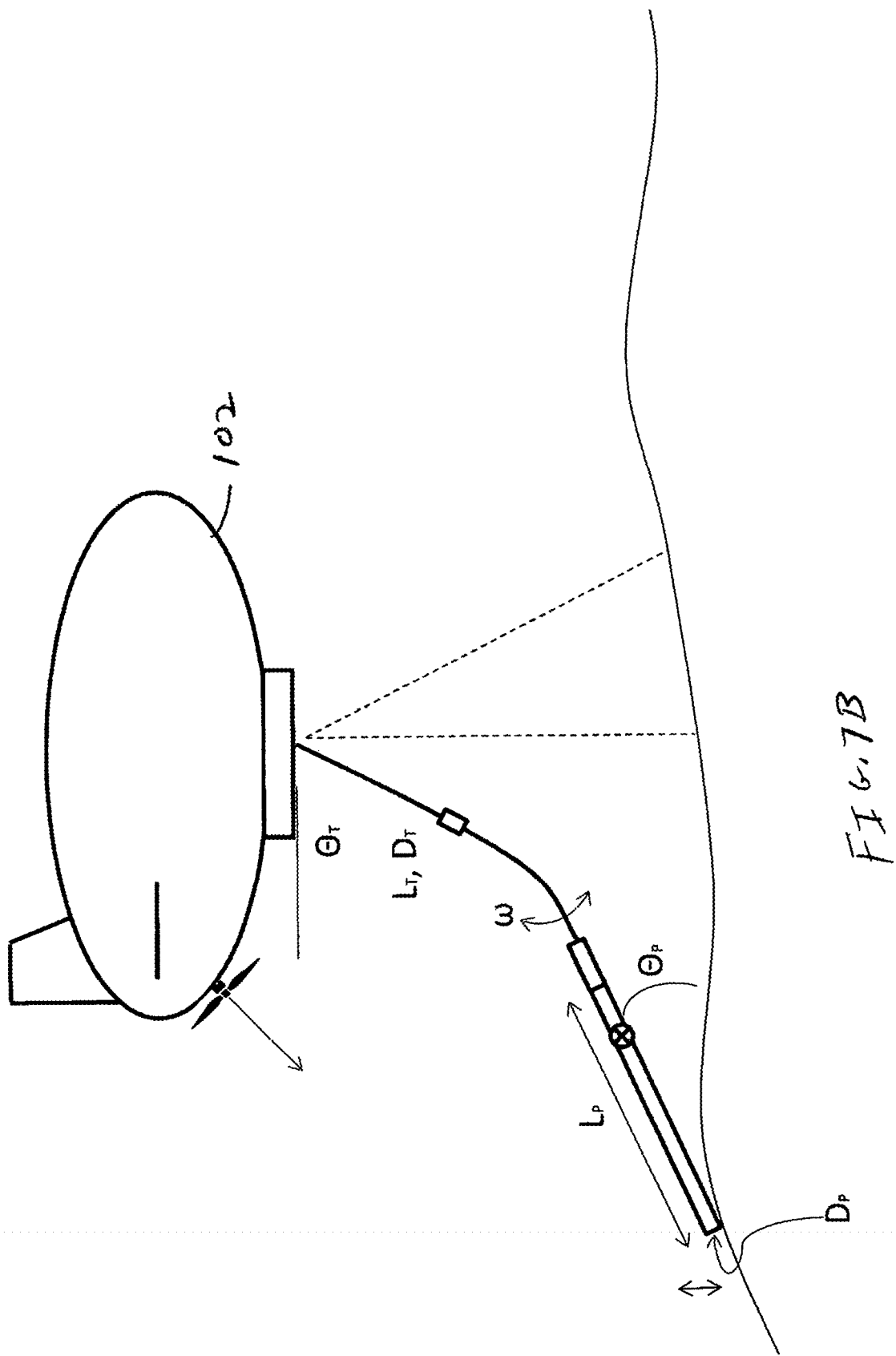

In the example embodiments of FIGS. 7A and 7B (quadcopter and lighter-than-air embodiments, respectively), UAV 102 is flying over variable terrain at a specific above ground height H1. Attached to the bottom side of the UAV 102 are the gas sensor, processor, navigational aids and LIDAR (not shown). A flexible tube 700 is attached to the gas sensor and to a fixed point on the UAV so that any tension or torque applied to the tube will be directed into the airframe of the UAV and not the joint between the tube and gas sensor.

The relevant tube properties are: length (e.g., 4 meters), inner diameter (e.g., 3/16"), outer diameter (i.e. 5/16"), durometer (i.e. 40A), surface roughness (i.e. 20 microns), etc Attached to the far end of the tube is a rigid section 702 the relevant properties of the rigid section are length (e.g., 1 meter), inner diameter (e.g., 0.5"), surface roughness, (e.g., 20 microns), weight (e.g., 1 lbs), etc. In example embodiments the far, or distal, end of the rigid section may be drug along the ground a substantial portion of the sampling time, a nozzle may fitted on the dragged end to serve as a replaceable wear component. The attachment between the flexible and rigid sections may be a hose fitting that allows for several degrees of rotational freedom. Example embodiments may include various combinations of flexible and rigid sections of tube, with the distal end terminating in either rigid or flexible sections. In example embodiments, a tube terminating at its distal end in a flexible section may be relatively short, allowing for some accommodation of terrain variation while avoiding the bouncing effect observed with a completely flexible tube.

When a vacuum is applied by the gas sensor pump to the UAV side of the tube 700, air is transported from ground-level at the far end of the rigid tube up through the fittings, and flexible tube to the gas sensor for analysis. The flow rate of the vacuum in the sensor as well as the diameters, surface roughness, and lengths of all the elements in the fluid path (flexible and rigid tube fittings) define the time required for samples to reach the sensor after being pulled into the tube. A commercially available detector with embedded pump coupled to an inlet tube composed of a 3 foot rigid section of carbon fiber tube of ½ inch inner diameter, 20 micron interior surface roughness, weight of 1 pound coupled to a 12 foot flexible section of 3/16 inch inner diameter, 5/16 inch outer diameter vinyl tubing with interior surface roughness less than 20 microns resulted in methane samples reaching the detector in approximately 4 seconds after entering the distal end of the sampling tube.

One sampling method in accordance with principles of inventive concepts entails analyzing the same volume of gas per linear foot of terrain traversed, such that the sampling frequency per foot is consistent. On a flat terrain this simply requires a constant flight velocity and steady altitude. Above varying terrain, a constant altitude would result in a higher sampling frequency for increasing slopes and lower sampling frequency for decreasing slopes. To avoid such inconsistency, the UAV may fly at a constant above ground level (AGL) to maintain constant sampling frequency.

Maintaining a consistent AGL may be accomplished in accordance with principles of inventive concepts via a laser range finder mounted on the UAV, generally pointing in the downward direction. A closed loop control system receives the current AGL reading from the laser range finder, compares it to the desired AGL, and throttles the propeller speed up or down to modify the UAV AGL to better match the desired AGL. The laser range finder can also be pointed along the direction of travel such that the range finder is providing the distance to a point slightly in ahead of the path of the UAV, which, combined with previously stored range finder measurements and associated forward looking angles, allows for a 2D map of the upcoming terrain to be created, such that the UAV can anticipate changes in terrain and throttle prop speed to preemptively accommodate terrain changes and maintain consistent AGL.

The location of the sample inlet with respect to the UAV is a function of the lengths of all the elements, stiffness of all the elements, the height of the UAV, maximum rotation allowed at the attachment point between the UAV and tube and the rotational fitting between the flexible and rigid tube sections, the amount of friction on the dragged tube end, the terrain traversed, and the flight path of the UAV. From these variables, the delta in position between the UAV GPS and the inlet to the tube can be calculated. Lateral force applied by the UAV to incur forward movement in the direction of desired sampling acts on the sampling tube at AGL, while a frictional force created between the dragged end of the sampling tube and the ground acts at ground level, creating tension in the sampling tube. The vector of the tension force at the attachment point of the sampling tube to the UAV, $\Theta_T$, is influenced by the geometric and material properties of the elements in the sampling tube resulting in curvature of the flexible section of the sampling tube and the allowed angular deflection in flexible coupling between the rigid and flexible section of sampling tube. A flexible section of sampling tube with a high durometer ($D_T$), large difference between interior and outer diameter and short length ($L_T$) coupled to a relatively light weight rigid element of the sampling tube will result in a small degree of curvature in the flexible section of the sampling tube; while a flexible tube with inverse properties will result in larger degree of curvature in the flexible section of the sampling tube. The summation of the angular curvature of the flexible element of the sampling tube, angle of tension vector and angle created between the rigid element of the sampling tube and ground ($\Theta_P$) will nominally sum to 90 degrees minus the angle of ground with respect to flat. The net lateral delta in position of distal end of the sampling tube to the UAV is calculated as a summation of the lateral components of the length of elements in the sampling tube. One study including a rigid section sampling tube composed of a 3 foot length of carbon fiber tube of ½ inch inner diameter, weight of 1 pound coupled to a 12 foot flexible section of 3/16 inch inner diameter, 5/16 inch outer diameter vinyl tubing of durometer 40A and flexible element allowing 15° of angular misalignment between the flexible and rigid elements of the sampling tube showed a lateral offset of 6 feet, which correlated within measurable tolerances to an experimental setup fo the same parameters.

In landfill applications in accordance with principles of inventive concepts, sampling is performed and no more than a prescribed height above the ground, 4 inches for example. As UAV 102 pulls the tube 702 across the ground, a simple weighted end may have a tendency to catch on the ground and then jump forward to another location where it catches again and/or incur large upward velocities upon impact with relatively small objects (such as rocks, bumps, tubes, etc). In example embodiments rigid tube 702 at the distal end of the sample inlet rotates with angular velocity ω at the flexible couple disposed between the flexible and rigid elements of the sampling tube as shown in the diagram of FIG. 7A or in embodiments without said flexible couple, rotation occurs within the flexible portion sampling tube. If the end of the tube 702 catches or impacts a relatively small object, it is less likely to violently jump, as the energy input to the full tube is both rotational as well as translational (up and forward for violently jumping) whereas the energy input to a point mass is solely translational. Should the distal end of the rigid tube catch, the tube may rotate near the connection point to the flexible tube, but the maximum upwards translation of is minimal and the distal end quickly falls back to the ground. This indicates that the rigid section 702 itself does not need to have significant mass given an adequate length; furthermore, the distribution of the mass of the rigid section does not need to be uniform if it implies adequate resistance to rotation Prop wash may be a factor in collecting gas samples in a UAV gas detection system 100 in accordance with principles of inventive concepts, as illustrated conceptually in the diagram of FIG. 8. UAV prop wash may be a factor in the dispersion of air at the ground-level (ground effect). Better gas readings may be obtained if the tube inlet (that is, distal end of tube 702) traverses only terrain surface that has not (yet) been subjected to the prop wash. When flying the UAV 102 in a straight line, the UAV may be angled in the direction of motion proportional to the speed of the UAV, such that the faster the UAV travels the further behind the UAV the prop wash impacts the ground; the speed of the UAV in the plane of the terrain should be large enough that the distal end of the sampling tube will traverse a point of terrain prior to the prop wash reaching that same point of terrain. Otherwise, the prop wash of the UAV has the potential to disperse at least a portion of the ground-level gas, resulting in a peak measurement lower than if the measurement had not been affected by propwash.

When the UAV is simply flying in a straight line and constant AGL, the prop wash may impact the terrain along the same line. Over varying terrain, the time between the UAV flying over a point on the terrain and propwash impacting that same point varies based on the slope of the terrain and the change in lift force (propwash volume flow rate—speed) required to maintain AGL.

During turns, neither the location the prop wash impacts the terrain, nor the path of the dragged tube inlet will follow the flight path of the UAV. Rather, both will be offtracked from the flight path, in a similar way to how a trailer does not follow the path of a car pulling it around a corner. The offtracking is advantageous to minimize the intersection of the terrain impacted by propwash and the path of the dragged tube inlet. This effect is illustrated by the inlet position (broken line), flight path (squared line), and prop wash vector locations illustrated in FIG. 8.

Figure 8:
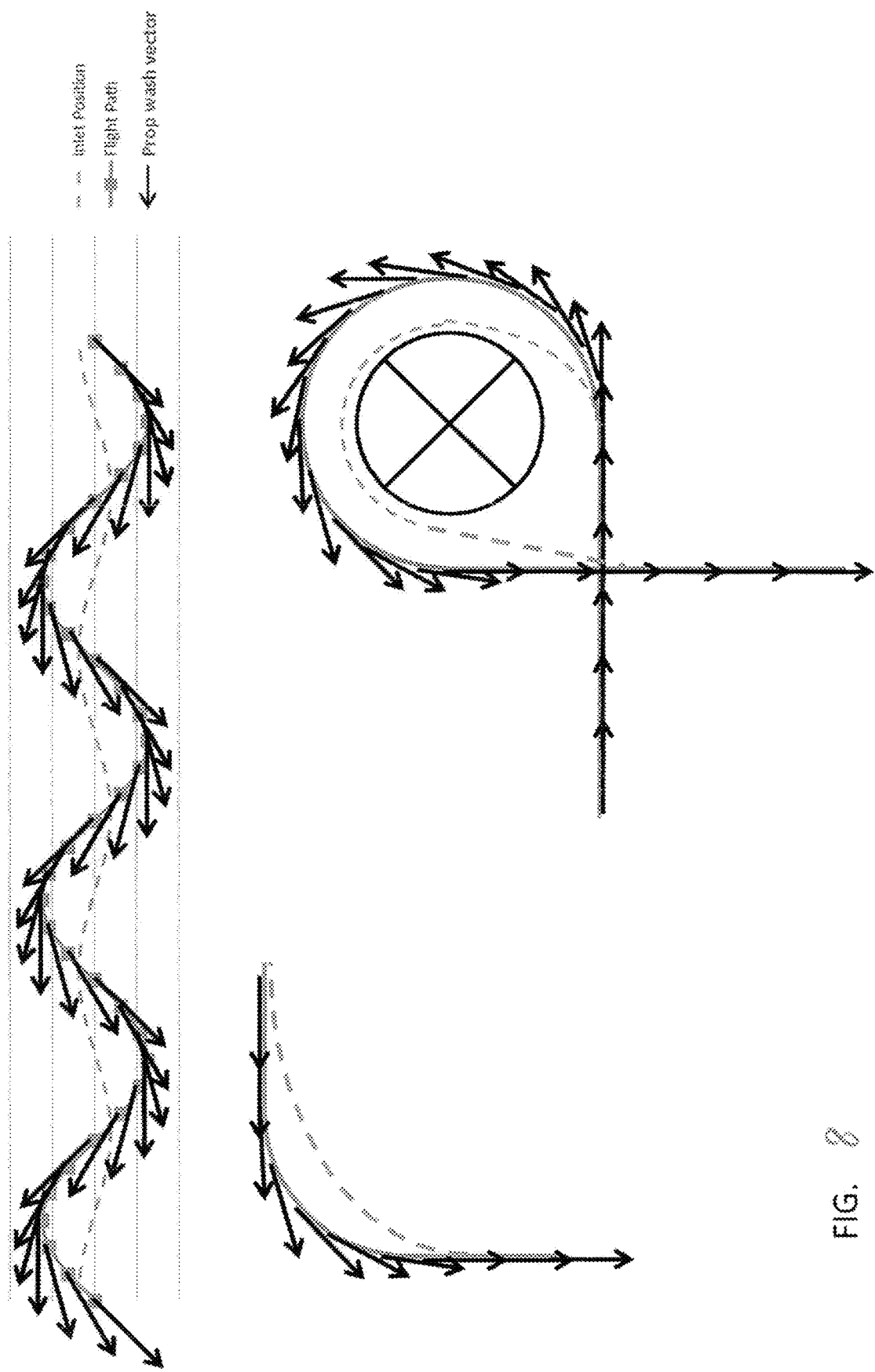
FIG. 8 is an example diagram illustrating prop wash in relation to flight paths.

In example embodiments, by flying in a concentric circle with a larger diameter than the point/area of interest, the tube will be offtracked towards the center of the circle (smaller diameter), while the propwash will be directed tangentially and affect ground along a larger diameter circle. Special points of interest could include: dead grass, tube inlets, tube outlets, disturbed ground, disturbed ground covering, well heads, foreign objects, rocks, stakes, markers, man-made objects, vehicles, buildings, trash, etc. Although a circular path is depicted in FIG. 8, the shape can of many different geometries, as long as the flight path goes around the object with some portions of curvature to offtrack to the tube inlet to the inside. With respect to the rectilinear flight path of FIG. 5B, the substantially parallel elements of the flight path may be replaced with slightly sinusoidal elements to offtrack the propwash away from the path traversed by the distal end of the sampling tube.

In example embodiments a method entails dragging a flexible environmental sample collection tube from an aerial vehicle at a constant height that is less than the length of the environmental sampling tube, interrupting the flight path at defined intervals to increase the altitude of the aerial vehicle to a height equal to the length of the tube, collecting a sample that is directly beneath the unmanned aerial vehicle while simultaneously sampling the global positioning data from the aerial vehicle, followed by continuing along the desired heading while decreasing altitude back to below the length of the environmental sampling tube.

In a similar method, a high degree of awareness of the environmental sample location is achieved when changing the bearing of the aerial vehicle by approaching the desired turning point, raising the aerial vehicle to a height above the surface terrain equal to the length of the flexible environmental sample collection tube, optionally gathering an environmental sample and sampling GPS data at this peak position, then pivoting the vehicle to the new heading and proceeding along that heading while simultaneously decreasing altitude back to a height less than the environmental sampling tube.

In a similar method a sample is taken from beneath an obstruction by dragging a flexible environmental sample collection tube from an aerial vehicle at a constant height that is less than the length of the environmental sampling tube, increasing the height of the unmanned aerial vehicle to the length of the environmental sampling tube while approaching the obstacle, allowing the environmental sampling tube to impact said obstacle which will act as a bending point for the sampling tube, and simultaneously halting the forward progress and decreasing the altitude of the unmanned aerial vehicle to rest the inlet of the environmental sampling tube on the ground beneath the obstacle during its pendulum like action pivoting around the bend point, collecting an environmental sample and optionally recording either the location of the obstruction or the GPS location of the unmanned aerial vehicle.

In a similar method, a sample is taken in close proximity to tall vertical obstacle comprising, dragging a flexible environmental sample collection tube from an aerial vehicle at a constant height that is less than the length of the environmental sampling tube, increasing the height of the unmanned aerial vehicle to the length of the environmental sampling tube while approaching the tall vertical obstacle, abruptly halting the forward progress of the unmanned aerial vehicle, allowing the tube to momentum to swing forward to a more forward position than the unmanned aerial vehicle, decreasing the altitude of the unmanned aerial vehicle to rest the inlet of the environmental sampling tube on the ground in a position closer to the vertical wall than half the width of the unmanned aerial vehicle.

Furthermore, a method of taking ground-level environmental samples with a high degree of locational accuracy through a semi permeable obstruction (like a bush or hedge) comprises dragging a flexible environmental sample collection tube from an aerial vehicle at a constant height that is less than the length of the environmental sampling tube, increasing the height of the UAV to the sum of the height of the environmental sampling tube and the semi permeable obstruction, pausing the forward progress of the unmanned aerial vehicle when the sampling tube is vertical and directly above the semi-permeable obstruction, decreasing the height of the unmanned aerial vehicle above ground-level to the length of the environmental sampling tube, collecting an environmental sample and sampling the GPS location of the unmanned aerial vehicle.

In the above outlined methods, it is noted that the location of the inlet to the environmental sampling tube is dissociated from the GPS unit in the unmanned aerial vehicle. This issue is alleviated by tracking the inlet to the environmental sampling tube from the unmanned aerial vehicle, from a camera for example; knowledge of the current above ground height of the unmanned aerial vehicle, angle of the camera centered on the inlet of the environmental sampling tube, and elevation profile data of the previously traversed terrain, the precise location of the environmental sampling tube inlet can be calculated.

One challenge in adapting the state of the art UAVs for taking continuous near ground environmental samples is the dissociation of the sampling tube inlet from the detector; in a manual operation the tube length is mostly dependent upon anthropomorphic distances from a waist or back mounted detector with GPS to the ground, while the tube length when the detector is carried on a UAV will need to increase given the state of the art UAVs inability to avoid ground collisions at very low altitudes. A longer sampling tube introduces larger than typical offset errors corresponding to sample transport time through the sampling tube; additionally, the position of the sampling tube inlet can now be further from the location recorded by the GPS leading to offset errors that are dependent on unpredictable UAV height above variable surface terrain.

In example embodiments, a UAV (i.e. quadcopter, traditional helicopter, coaxial counter-rotating helicopter, fixed wing plane, tricopter, motor-assisted lighter-than-air vehicle, etc.) gathers environmental samples at or near ground-level through the use of an environmental sampling tube with an inlet disposed at ground-level and attached at the other end to the unmanned aerial vehicle at an above ground altitude.

Figure 9:
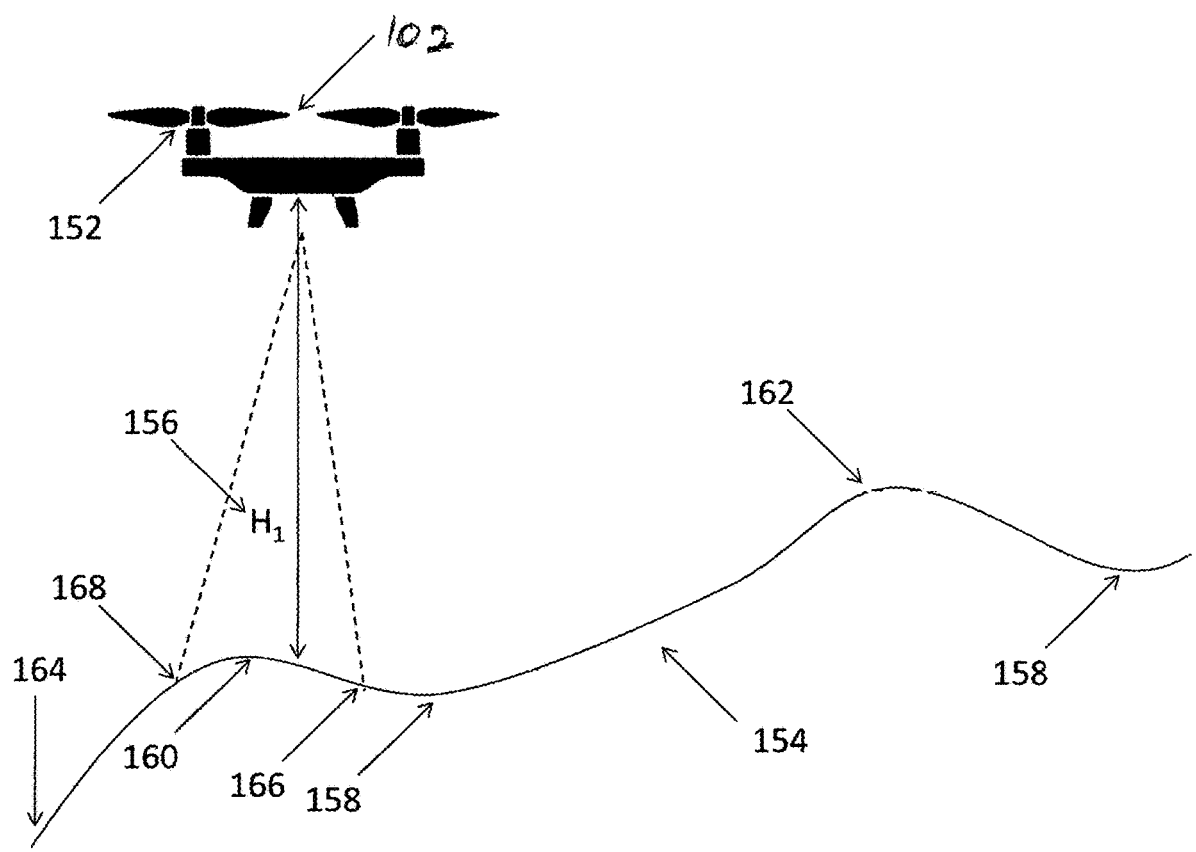
FIG. 9 is an example diagram of an unmanned aerial detector in operation in accordance with principles of inventive concepts over a varying terrain.

An UAV in flight above ground has several relevant parameters; referring to FIG. 9, an UAV 102 is in flight via one or more rotors 152 above ground 154 at a height 156. The ground with potential for variable surface terrain 154 may include one or more relative minimums 158 and relative maximums 160, as well as a global maximum within a specified area 162 and a global minimum within a specified area 164. The UAVs height above ground is really an approximation with uncertainty associated with the variable terrain within a cone of analyzed terrain depicted two dimensionally with 166 and 168.

Uncertainties in above ground height 156 combined with variable surface terrain 154 make it exceedingly difficult to maintain the inlet of the environmental sampling at ground-level. A human arm and brain create a precise control system with a multitude of actuators to continually adjust the location of the inlet to ground-level, an UAV has only the rotors 152 to incur all movement at the inlet of the environmental sampling tube 118.

Figures 10A, 10B:
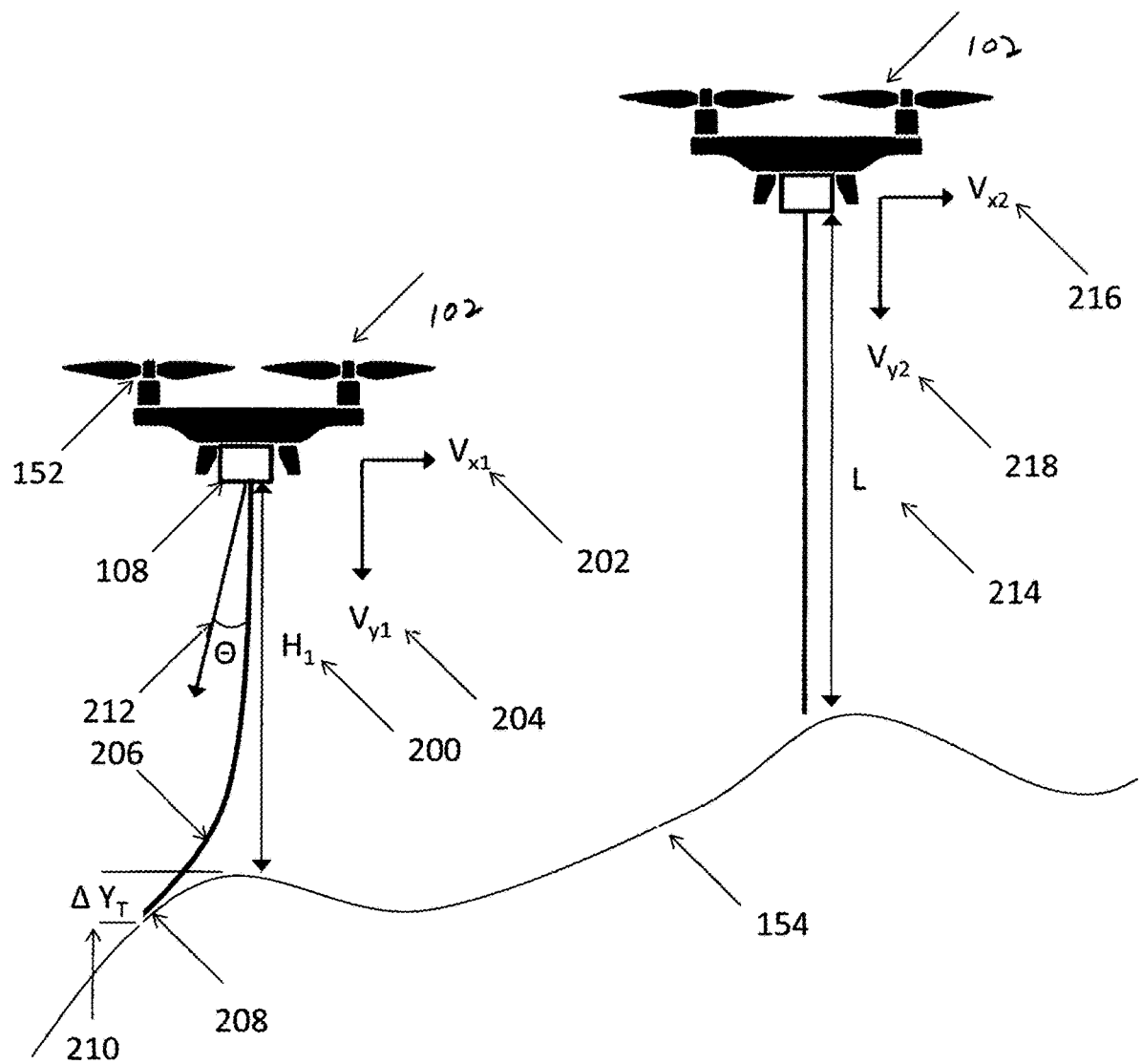
FIGS. 10A and 10B are diagrams of an unmanned aerial detector in operation in accordance with principles of inventive concepts over a varying terrain.

To overcome the aforementioned lack of a human-like control system, in an example embodiment depicted in FIG. 10a shows the system of the invention with an UAV 102 flying via the use of a multiplicity of rotors 152. In a narrowly defined snapshot of time, the UAV measures, through the use of onboard sensors (i.e. sonar, lidar, etc.) the instantaneous above ground height 200 and measures the velocity with respect to either the air or the ground in the X direction 202 and measures the velocity with respect to either the air or the ground in the Y direction 204 via additional on board sensors (i.e. GPS, barometer, pitot static tube, ground-level imaging, accelerometers, etc.). The UAV is carrying a receiving unit 108 which is coupled to long flexible environmental sampling tube 206. The height 200 above a variable surface terrain 154 is controlled a computer based control system on the UAV increasing or decreasing the power allocated to the rotors 152 to keep the height 200 less than the total length of the flexible environmental sampling tube 206. In this way, the inlet of the environmental sampling tube 208 is defined by the control system to be dragged on the variable surface terrain 154. Due to variations in the surface terrain and the delta in height between the above ground height of the UAV 200 and the length of the environmental sampling tube, there will be difference between the measured above ground height of the UAV 200 and the height from the UAV above the inlet of the environmental sampling tube 208; this delta is defined as a delta Y of the tube inlet 210.

With the inlet of the environmental sampling tube 208 dragged along the variable surface terrain 154, any location data gathered by the UAV (i.e. calculated from acceleration sensors, calculated from velocity sensors, recorded from ground imaging sensors, global positioning systems, triangulation from known points via RFID, etc) will not accurately define the location of the inlet of the environmental sampling tube 208. The delta is calculated by incorporating a system to measure the angle of a ray drawn from the UAV 102 and the inlet of the environmental sampling tube 208, shown as 212, and recording the measured above ground height of the UAV 102 as it traversers the variable surface terrain. The system to measure 212 will incorporate a means to track the inlet, such as image recognition, RFID triangulation, etc. The position of the inlet of the environmental sampling tube 208 with respect to the UAV 102 can then be calculated from the measured angle 212, the currently recorded above ground height 200, the recorded surface topology previously traversed by the UAV (yielding the calculation of 210) and knowledge of the stiffness of the environmental sampling tube.

The above calculation will provide the desired location data to correlate to an environmental sample received from inlet of the environmental sampling tube inlet 208, transported within the environmental sampling tube 206 to the receiving unit 108 attached to the UAV. When gathering a multiplicity of environmental samples, for instance continuous sampling, a temporal offset may need to also be added to account for the transport time of the sample as it travels the length of the environmental sampling tube 206 and analysis or transport to storage system within the receiving unit 108. This embodiment successfully correlates an environmental sample inlet location to the UAV. This method, however may still include errors associated accumulated with the numerous sensors involved and compounded with sensor inaccuracies that are typical much larger during dynamic events versus static measuring scenarios. An alternate method utilizing the same system as the prior embodiment to increase the precision of the knowledge of the environmental sampling tube inlet is thus presented.

In a physical system as described in FIG. 10a, the flight plan of the UAV is defined to also include moments of high accuracy sampling by increasing the above ground height of the UAV 102 to be equal to the length of the environmental sampling tube, the height shown as 214. To minimize the errors incurred by the variable surface terrain and dynamic measurement errors, the X and Y components of the UAV's velocity, 216 and 218 respectively are brought as close to zero as possible. When the flight plan is arrested for a moment in this position, no planar delta exists between the location of the sampling tube inlet and the measured location of the UAV, so the recorded location for the environmental samples located during this pause in the flight path will have a high degree of accuracy. This position is not sustainable for continuous flight at high velocity due to the UAVs in ability to rapidly adjust the above ground height over variable surface terrain.

Figure 11:
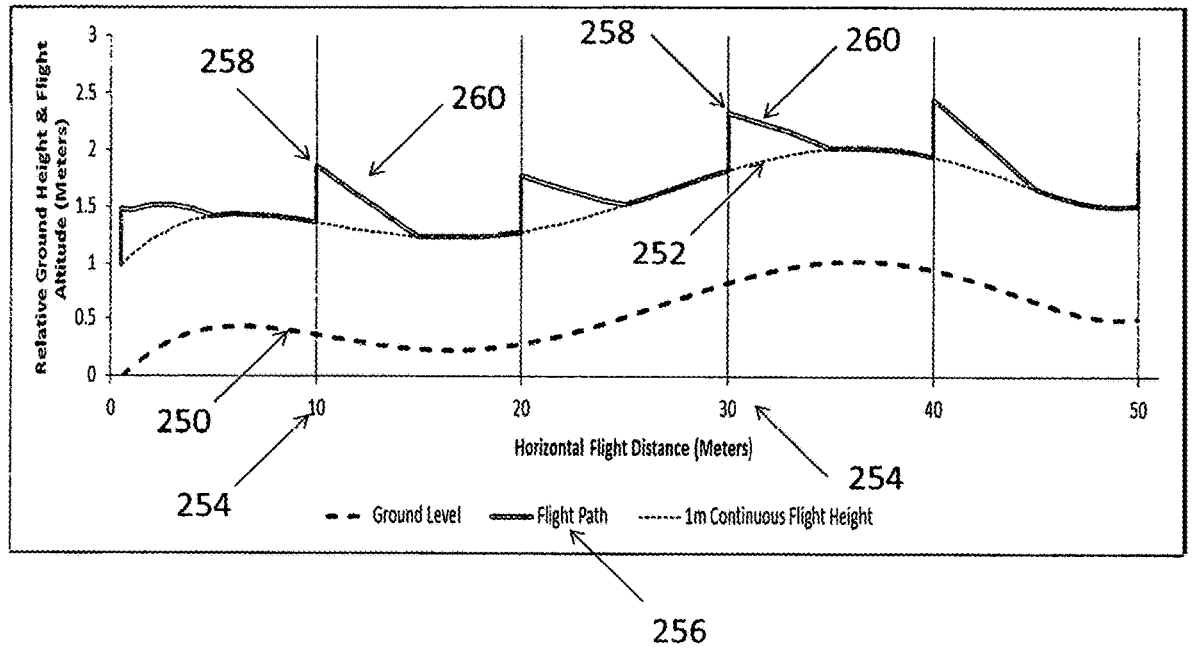
FIG. 11 is a chart depicting an example embodiment of a flight path in accordance with principles of inventive concepts.

An example embodiment flight plan for adding flight plan interrupts to collect data points with a high degree of location accuracy is shown in FIG. 11. The variable surface terrain is graphically depicted as 250 with a one meter offset depicted as 252 for the nominal flight path without interrupts for high accuracy sampling. At standard distance increments 254, the actual flight path 256 includes rapid ascent to a higher above ground altitude equal to the length of the environmental sampling tube 258, followed by a gradual decline in altitude back to the standard offset 260. Those skilled in the art will recognize that in continuous sampling, the presented method will increase the sampling density per linear unit in the direction of the flight path as the UAV ascends due to the inlet of the sampling tube less rapidly traversing the surface terrain during ascent to the altitude equal to environmental sample tube length versus standard traversing of variable surface terrain. Pausing the planar velocity of the UAV at the peaks of the flight plan 258 allows for recording sample location data that is not impacted by offsets in a dragged tube or errors due the dynamics of the standard method of collecting ground-level environmental samples.

Figure 12:
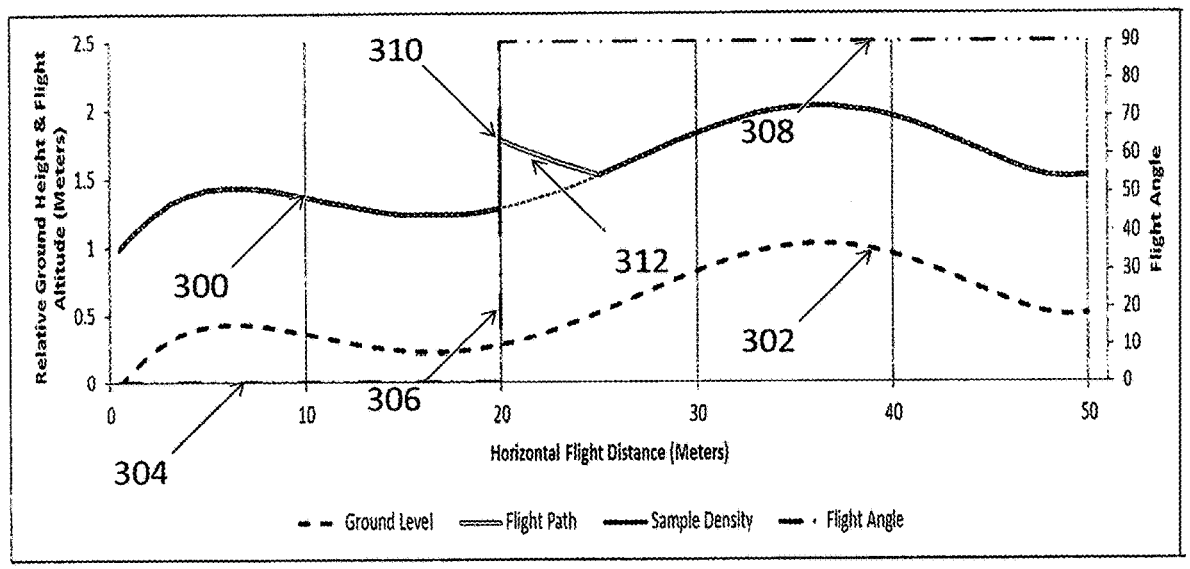
FIG. 12 is a chart depicting an example embodiment of a flight path in accordance with principles of inventive concepts.

The previously defined method leads to a corresponding method of modifying the orientation of the UAV without losing accurate location data for the location of collected ground-level environmental samples. FIG. 12 shows a graphical depiction of a flight plan 300 over variable surface terrain 302 at an original flight angle of zero degrees. At a defined place, the UAV requires the heading to be altered by ninety degrees, shown as a vertical line 306 traversing the zero degree flight angle 304 and the ninety degree flight angle 308. Modifying the flight angle in the system with an UAV dragging an environmental sampling tube would normally lead inaccurate location data associated with the sample due to the environmental sampling tube following a more rounded than the UAVs change in heading. For simplicity, this embodiment describes a sharp ninety degree change in flight angle with a well-defined vertex, but those skilled in the art will recognize that this is merely an example of a problem inherent in changing the direction of the UAV in more gradual turns at all angles.

To record ground-level environmental samples from a dragged environmental sampling tube carried by an UAV making a turn with a high degree of locational accuracy, the above ground height of the UAV is increased at the vertex of the turn to a height equal to the length of the environmental sampling tube; the UAV can then proceed back to a standard above ground offset 312 in the new flight angle without the inlet of the environmental sampling tube making a more rounded turn that the UAV with a hard to measure path.

Collecting ground-level environmental samples from an UAV must be able to traverse not just variable surface terrain, but also various obstructions in order to collect samples with a high degree of location accuracy from as many locations as possible. One such obstruction is an above ground obstacle with exposed variable terrain below the obstacle. FIGS. 12a-d depict the method for taking ground-level environmental samples from beneath an above ground tube, but those skilled in the art will understand that the above ground obstacle could be of any geometry and still leave overhung ground requiring sampling.

FIG. 12a shows the UAV 102 flying via the use of a multiplicity of rotors 152 and a height 350 less than the length of the environmental sampling tube 206, leading to the inlet of the environmental sampling tube 208 to be in constant close proximity to the ground for sample collection even over variable terrain 154 which leads to a vertical offset 210 between the environmental sampling tube inlet 208 and the measured distance to ground. The UAV is traveling in the X direction with known velocity in the X direction 352 over the variable surface terrain 154 at a constant height leading to constantly modulated velocity in the Y direction 354 to attempt to maintain a consistent above ground height 350. The unmanned aerial is approaching an obstacle 356 offset from ground-level at a distinct height 358.

FIG. 12b shows the first step in taking a ground-level environmental sample from beneath the above ground obstacle from the flexible environmental sampling coupled to the UAV. As the UAV approaches the above ground obstacle 356, the height of the UAV is increased such that the height equals the length of the sampling tube 360 by manipulating the velocity of the UAV in the Y direction 364; the velocity of the UAV in the X direction 362 may be decreased in order to increase height accuracy above variable surface terrain 154.

The next step is depicted in FIG. 12c; the UAV maintains a positive velocity in the X direction 400 towards the above ground obstacle 356, while modulating the vertical velocity of the UAV 402 to maintain a constant height equal to the length of the environmental sample tube length 360. Due to the positive velocity in the X direction toward the obstacle, 400, the flexible environmental sampling tube will impact the above ground obstacle. The location of the impact on the environmental sample tube 404, will be a function of the obstacle height above ground 358, the obstacle dimensions and the variable surface terrain. The location of the impact will act as a pivot point as the momentum of the inlet of the environmental sampling tube 208 continues to propel the inlet forward and underneath the obstacle in a pendulum like path 406.

The final step to collecting a ground-level environmental sample from beneath the above ground obstacle from the flexible environmental sampling coupled to the UAV is depicted in FIG. 12d and consists of modifying the velocity of the UAV in the Y direction 408 such that the inlet of the environmental sampling tube inlet 208 will touch and rest on the variable surface terrain 154 below the above ground obstacle 356. Simultaneously, the velocity in the X direction 410 is halted such that the inlet of the sampling tube 208 will be resting on the ground below the obstacle and have no force acting on it from the UAV velocity vectors to move it from the resting position. The environmental sampling tube 206 will most likely be touching the obstacle at the point of impact 404 and the inlet will be located at an offset in the X direction 412 from the location of impact and contact. A ground-level environmental sample can then be taken from beneath the obstacle via the environmental sampling tube.

A similar obstacle that can prevent ground-level sampling from an UAV is a vertical obstruction taller than the length of the environmental sampling tube. Without the method of this invention, the UAV would be prevented from sampling at ground points between one half the width of the UAV and the vertical obstruction (assuming a centrally mounted receiving unit). In a similar method to the above ground obstacle sampling, the environmental sampling tube is swung into a position normally inaccessible.

Figures 13A, 13B:
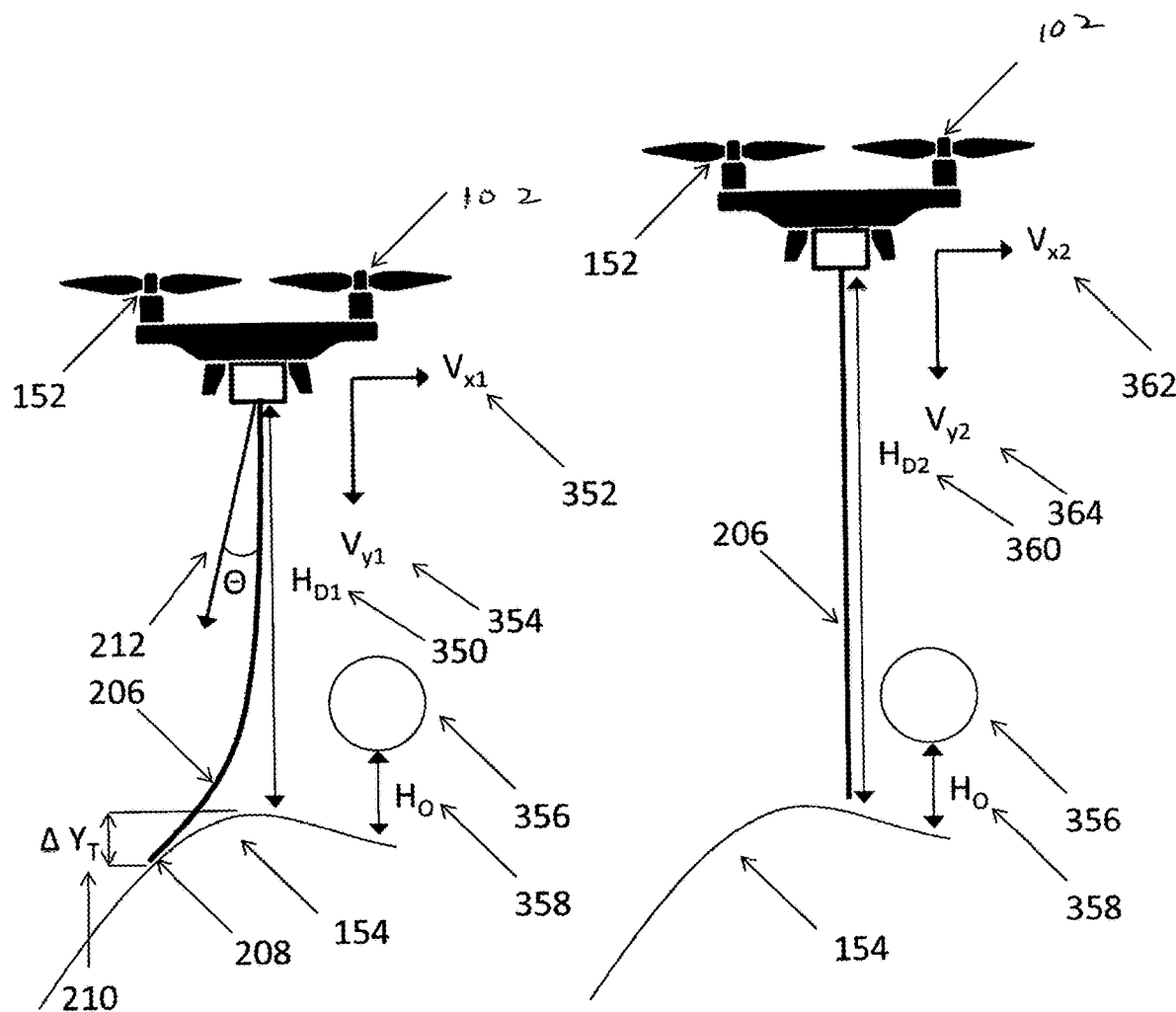
FIGS. 13a through 13d are diagrams of an unmanned aerial detector in operation in accordance with principles of inventive concepts over a varying terrain.

FIG. 13a shows the UAV 102 flying via the use of a multiplicity of rotors 152 and a height 350 less than the length of the environmental sampling tube 206, leading to the inlet of the environmental sampling tube 208 to be in constant close proximity to the ground for sample collection even over variable terrain 154 which leads to a vertical offset 210 between the environmental sampling tube inlet 208 and the measured distance to ground. The UAV is traveling in the X direction with known velocity in the X direction 450 over the variable surface terrain 154 at a constant height leading to constantly modulated velocity in the Y direction 452 to attempt to maintain a consistent above ground height 350. The unmanned aerial is approaching a vertical obstacle 454 which is taller than the length of the environmental sampling tube 206.

FIG. 13b shows the first step in taking a ground-level environmental sample within close proximity to a vertical obstruction taller than the length of the environmental sampling tube from the flexible environmental sampling coupled to the UAV. As the UAV approaches the vertical obstacle 454, the height of the UAV is increased such that the height equals the length of the sampling tube 360 by manipulating the velocity of the UAV in the Y direction 456; the velocity of the UAV in the X direction 458 may be decreased in order to increase height accuracy above variable surface terrain 154.

Figures 13C, 13D:
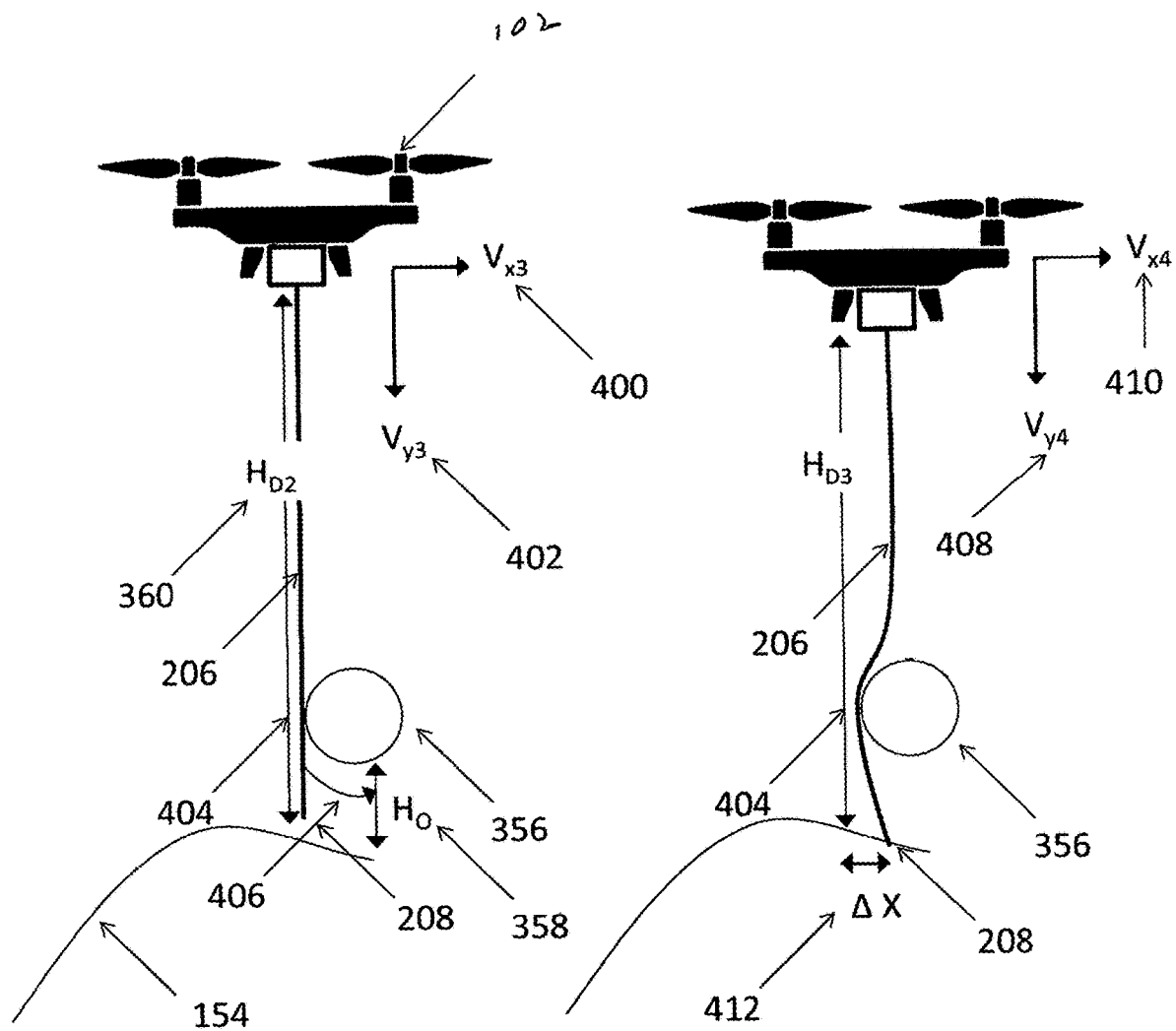

The next step is depicted in FIG. 13c; the UAV abruptly reduces velocity in the X direction 500 towards the vertical obstacle 454 to or near zero, while modulating the vertical velocity of the UAV 502 to maintain a constant height equal to the length of the environmental sample tube length 360. Due to the abrupt reduction in velocity in the X direction toward the obstacle, 500, the momentum of the flexible environmental sampling tube continue to propel the inlet of the environmental sampling tube 208 toward the vertical obstacle 454 in a pendulum like trajectory 504.

Finally, as depicted in FIG. 13d, the height of the UAV 506 is decreased by modifying the velocity in the Y direction 508 such that the inlet of the environmental sampling tube 208 rests on the variable surface terrain 154 in close proximity to the vertical obstruction 454. Specifically, the inlet of the environmental sampling tube 208 is closer to the vertical obstruction than half the width of the UAV 102. A ground-level environmental sample can then be taken from within close proximity to the vertical obstacle via the environmental sampling tube.

A similar obstacle that can prevent ground-level sampling from an UAV is a semi permeable obstruction that prevents the sample tube from reaching ground-level when being drug laterally across the obstacle, but is permeable enough that the tube diameter would not normally be completely prevented from reaching ground-level.

Figures 14A, 14B:
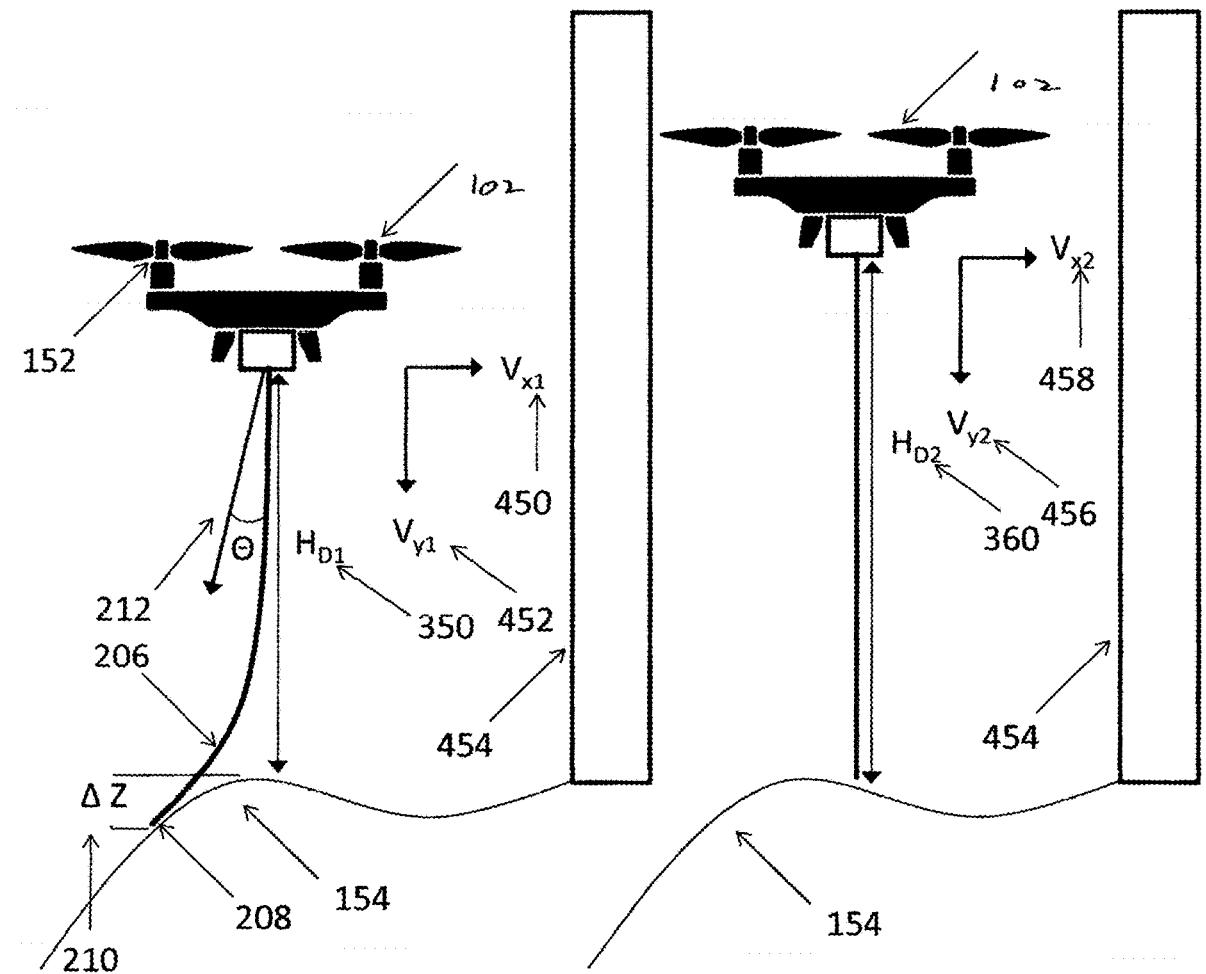
FIGS. 14a through 14d are diagrams of an unmanned aerial detector in operation in accordance with principles of inventive concepts.

FIG. 14a shows the UAV 102 flying via the use of a multiplicity of rotors 152 and a height 350 less than the length of the environmental sampling tube 206, leading to the inlet of the environmental sampling tube 208 to be in constant close proximity to the ground for sample collection even over variable terrain 154 which leads to a vertical offset 210 between the environmental sampling tube inlet 208 and the measured distance to ground. The UAV is traveling in the X direction with known velocity in the X direction 550 over the variable surface terrain 154 at a constant height leading to constantly modulated velocity in the Y direction 552 to attempt to maintain a consistent above ground height 350. The unmanned aerial is approaching a semi-permeable obstacle 554. The semi-permeable obstacle is such that an environmental sampling tube could be drug across the top without the inlet permeating down to ground-level, but open enough that the tube diameter inserted vertically would be able to permeate to ground-level. In other works, the openness of the permeable object is not great enough to allow a length of tube to reach ground-level, but is enough for a diameter of tube to reach ground-level.

FIG. 14b shows the first step in taking a ground-level environmental sample within a semi-permeable from the flexible environmental sampling coupled to the UAV. As the UAV approaches the semi-permeable obstacle 554, the height of the UAV is increased such that the height equals the length of the sampling tube 360 by manipulating the velocity of the UAV in the Y direction 556; the velocity of the UAV in the X direction 558 may be decreased in order to increase height accuracy above variable surface terrain 154.

Figures 14C, 14D:
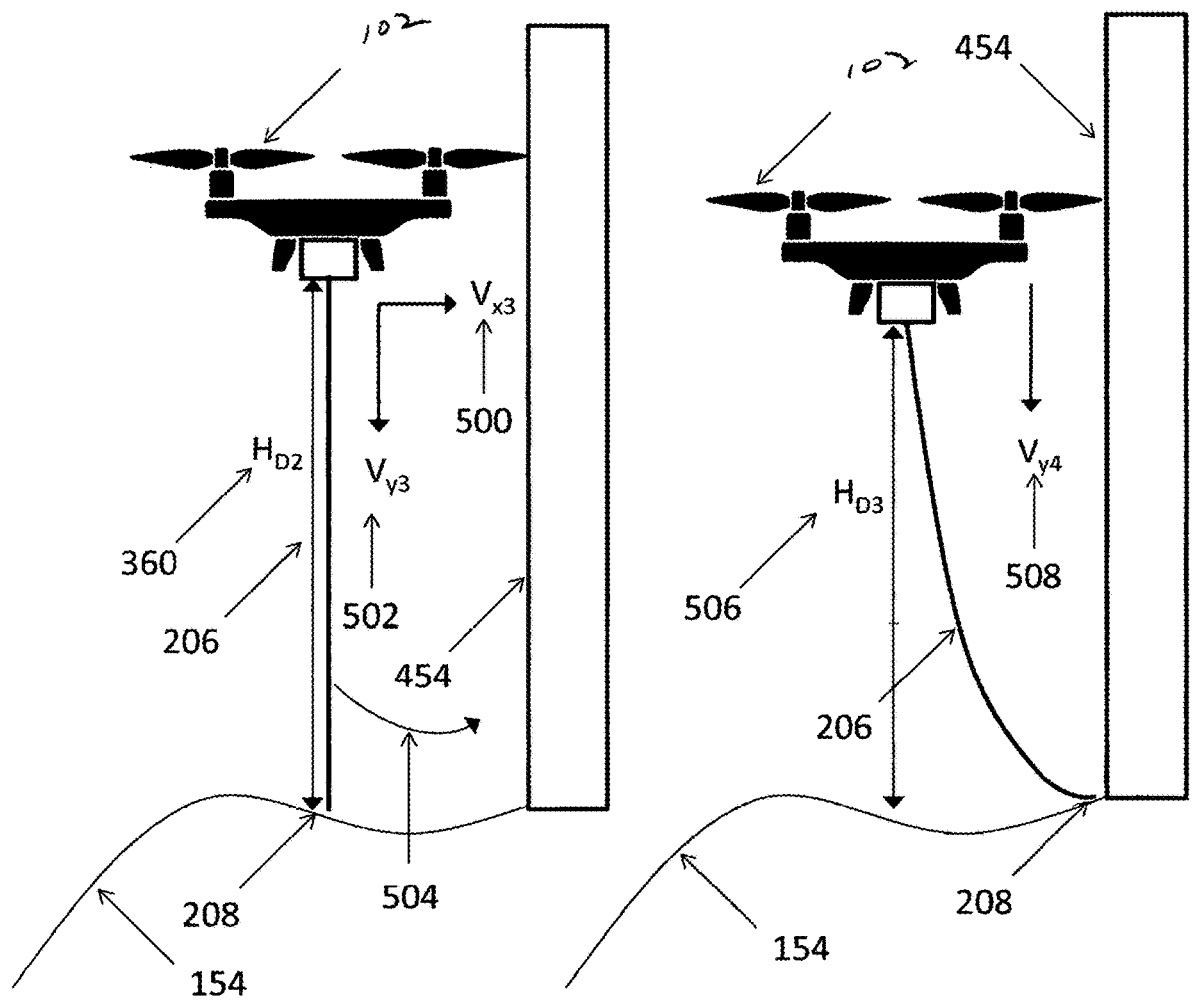

The next step is depicted in FIG. 14c; the UAV increases velocity in the Y direction 600 to position the UAV such that the height of the UAV 602 is equal to the length of the environmental sampling tube plus the height of the semi-permeable obstruction 604. The X direction velocity 606 is maintained until the UAV is positioned directly on top of the desired point of interest at the base of the semi-permeable obstruction. It will be apparent to those skilled in the art that while the semi-permeable obstruction is illustrated as an object with a flat base, the semi-permeable obstruction could also have variable bottom topology allowing ground-level surface terrain to not be flat and the height of the UAV is thus positioned with respect to the terrain beneath the semi-permeable object.

Finally, through modulation of UAV rotor power, the velocity in the Y direction of the UAV 608 modifies the height of the UAV 610 is reduced such that the inlet of the environmental sampling 208 permeates the semi-permeable obstruction and reaches ground-level. A ground-level environmental sample can then be taken from within the semi-permeable obstacle via the environmental sampling tube carried by the UAV.

While the present inventive concepts have been particularly shown and described above with reference to exemplary embodiments thereof, it will be understood by those of ordinary skill in the art, that various changes in form and detail can be made without departing from the spirit and scope of inventive concepts as defined by the following claims.

What is claimed is:

1. An unmanned aerial vehicle detector, comprising: an unmanned aerial vehicle; a pump/detector combination on the unmanned aerial vehicle; and a tube including a rigid section at a distal end and a flexible section connected at a proximal end to the pump/detector combination, wherein the pump/detector combination is configured to draw gas samples through an inlet formed at the distal end of the tube to the detector and to detect a level of a gas drawn from within a prescribed distance above ground level, the tube including a transition from rigid to flexible sections and the transition between flexible and rigid sections of the tube configured and arranged to act as a hinge, allowing the inlet to be moved along a surface of interest for gas sampling.

2. The unmanned aerial vehicle detector of claim 1, further comprising: a geolocation unit configured to determine the geolocation of the unmanned aerial vehicle; and a controller configured to determine the location from which a gas sample is obtained.

3. The unmanned aerial vehicle detector of claim 2, further comprising: an imager configured to image terrain proximate the unmanned aerial vehicle, wherein the controller is configured to corelate imagery obtained from the imager to a gas sample obtained through the tube.

4. The unmanned aerial vehicle detector of claim 3, wherein the imager is a visible light detector.

5. The unmanned aerial vehicle detector of claim 3, wherein the imager is an infrared detector.

6. The unmanned aerial vehicle detector of claim 2, wherein the controller is configured to direct the unmanned aerial vehicle detector along a course that surveys a tract satisfying a maximal sample-separation course requirement.

7. The unmanned aerial vehicle detector of claim 6, wherein the controller is configured to redirect the unmanned aerial vehicle along a localization course, whereby the source of gas emission may be more precisely located, when the detector detects a gas of interest at a level that exceeds a threshold.

8. A gas sampling method, comprising: an unmanned aerial vehicle flying over a tract of interest; and a pump/detector combination on the unmanned aerial vehicle drawing gas samples through a tube including a rigid section at a distal end and a flexible section connected at a proximal end to the pump/detector combination, wherein the pump/detector combination is configured to draw gas samples through an inlet formed at the distal end of the tube to the detector and to detect a level of a gas drawn from within a prescribed distance above ground level, the tube including a transition between rigid and flexible sections and the transition between flexible and rigid sections acting as a hinge to allow the inlet to be moved along a surface of interest for gas sampling.

9. The gas sampling method of claim 8, further comprising: a geolocation unit determining the geolocation of the unmanned aerial vehicle; and a controller determining the location from which a gas sample is obtained.

10. The gas sampling method of claim 9, further comprising: an imager imaging terrain proximate the unmanned aerial vehicle, the controller correlating imagery obtained from the imager to gas samples obtained through the inlet.

11. The gas sampling method of claim 10, wherein the imager images in visible light detector.

12. The gas sampling method of claim 10, wherein the imager images in an infrared light.

13. The gas sampling method of claim 9, wherein the controller directs the unmanned aerial vehicle detector along a course that surveys a tract satisfying a maximal sample-separation course requirement.

14. The gas sampling method of claim 13, wherein the controller redirects the unmanned aerial vehicle along a localization course, whereby the source of gas emission may be more precisely located, when the detector detects a gas of interest at a level that exceeds a threshold.

15. An unmanned aerial vehicle gas detecting system, comprising:

an unmanned aerial vehicle, including: a pump/detector combination on the unmanned aerial vehicle; a tube including a rigid section at a distal end and a flexible section connected at a proximal end to the pump/detector combination, wherein the pump/detector combination is configured to draw gas samples through an inlet formed at the distal end of the tube to the detector and to detect a level of a gas drawn from within a prescribed distance above ground level, the tube including a transition between flexible and rigid sections, the transition configured to act as a hinge to allow the inlet to be moved along a surface of interest for gas sampling; a wireless communication system;

and an external controller configured to receive gas detection data transmitted from the unmanned aerial vehicle and to store the gas detection data.

16. The unmanned aerial vehicle gas detection system of claim 15, wherein the external controller is configured to track gas detector data for a plurality of detection sessions.

17. The unmanned aerial vehicle gas detection system of claim 15, wherein the external controller is configured to receive imaging data from the unmanned aerial vehicle.

18. The unmanned aerial vehicle gas detection system of claim 17, wherein the external controller is configured to correlate imaging with gas detection data from the unmanned aerial vehicle.

19. The unmanned aerial vehicle gas detection system of claim 18, wherein the external controller is configured to correlate near infrared imaging data from the unmanned aerial vehicle with gas detection data from the unmanned aerial vehicle.

20. The unmanned aerial vehicle gas detection system of claim 15, further comprising: an unmanned aerial vehicle gas detection server.

* * * * *